(12) United States Patent
Enikov et al.

(10) Patent No.: US 7,959,570 B2
(45) Date of Patent: Jun. 14, 2011

(54) EYE TONOMETRY APPARATUS, SYSTEMS AND METHODS

(76) Inventors: Eniko Todorov Enikov, Tucson, AZ (US); Gholam Peyman, Sun City, AZ (US)

(*) Notice: Subject to any disclaimer, the term of this patent is extended or adjusted under 35 U.S.C. 154(b) by 0 days.

(21) Appl. No.: 12/807,101

(22) Filed: Aug. 27, 2010

(65) Prior Publication Data
US 2011/0054291 A1 Mar. 3, 2011

Related U.S. Application Data

(60) Provisional application No. 61/275,611, filed on Aug. 31, 2009.

(51) Int. Cl.
*A61B 3/16* (2006.01)
(52) U.S. Cl. ........................................... 600/398
(58) Field of Classification Search ........... 600/398–405
See application file for complete search history.

(56) References Cited

U.S. PATENT DOCUMENTS

| 4,523,597 | A | 6/1985 | Sawa et al. |
| 4,844,078 | A | 7/1989 | Pokhis |
| 5,830,139 | A | 11/1998 | Abreau |
| 6,579,235 | B1 | 6/2003 | Abita et al. |
| 6,981,946 | B2 | 1/2006 | Davidson |
| 7,004,902 | B2 | 2/2006 | Luce |
| 2004/0186367 | A1* | 9/2004 | Fresco ................ 600/398 |
| 2004/0267108 | A1* | 12/2004 | Moore ................ 600/398 |

* cited by examiner

*Primary Examiner* — Max Hindenburg
*Assistant Examiner* — Brian Szmal
(74) *Attorney, Agent, or Firm* — Francis Law Group

(57) ABSTRACT

A system for measuring intraocular pressure (IOP) of an eye, comprising a plurality of force sensors that are adapted to contact a surface of an eye, means for measuring the forces exerted on the force sensors when in contact with the eye surface, and processing means that is adapted to receive the measured forces and determine IOP of the eye as a function of the measured forces.

22 Claims, 13 Drawing Sheets

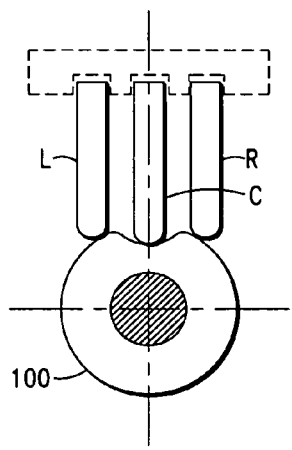 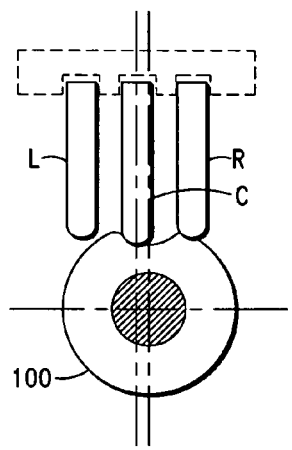 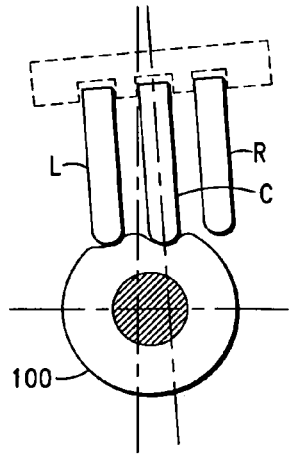
*FIG. 20A*  *FIG. 20B*  *FIG. 20C*
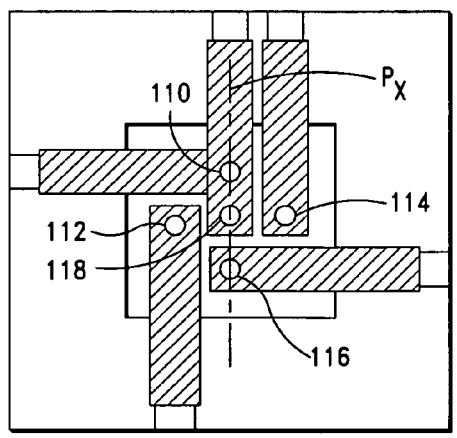 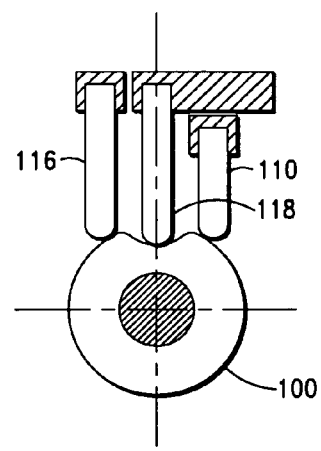
*FIG. 21A*  *FIG. 21B*

EYE TONOMETRY APPARATUS, SYSTEMS AND METHODS

CROSS-REFERENCE TO RELATED APPLICATIONS

This application claims the benefit of U.S. Provisional Application No. 61/275,611, filed Aug. 31, 2009.

FIELD OF THE PRESENT INVENTION

The present invention relates generally to systems and methods for measuring the intraocular pressure, i.e. the fluid pressure within an eye. More particularly, the invention relates to improved systems and methods for measuring intraocular or fluid pressure within an eye.

BACKGROUND OF THE INVENTION

As is well known in the art of ophthalmology, measuring the intraocular pressure (IOP) of the eye is an important indicator of the health of the eye. Elevated IOP has been associated with progressive damage of the optic nerve known as glaucoma, which, if left untreated, leads to permanent loss of sight.

Various apparatus and techniques have thus been developed to measure IOP. Among the techniques are applanation tonometery, dynamic contour tonometry, transpalpebral diatom tonometry, non-contact tonometry, electronic indentation tonometry, rebound tonometry and digital palpation tonometry.

Applanation tonometry measures approximate intraocular pressure either by the force required to flatten a constant area of the cornea (e.g. Goldmann tonometry) or by the area flattened by a constant force.

In applanation tonometry, a special calibrated disinfected probe attached to a slit lamp biomicroscope is used to flatten the central cornea a fixed amount. Because the probe makes contact with the cornea, a topical anesthetic, such as oxybuprocaine, tetracaine, alcaine, proxymetacaine or paracaine, is introduced onto the surface of the eye in the form of one or a few eye drops. A yellow fluorescein dye is often also used in conjunction with a cobalt blue filter to aid the examiner in determining the IOP.

Goldmann tonometry is considered to be the gold standard in tonometry, as it is the most widely accepted method of determining "approximate" intraocular pressure. However, as is well known in the art, Goldmann tonometry is an inherently imprecise measurement.

Dynamic contour tonometry (DCT) is a measuring technique that employs the principle of contour matching instead of applanation to eliminate the systematic errors inherent in previous tonometers. These factors include the influence of corneal thickness, rigidity, curvature and elastic properties. DCT is not influenced by mechanical changes, such as those seen in refractive surgery that would otherwise cause error in applanation tonometers.

An exemplar apparatus that employs DCT to measure IOP is the PASCAL Dynamic Contour Tonometer (Ziemer Ophthalmics). The PASCAL uses a miniature pressure sensor embedded within a tonometer tip that is contour-matched to the shape of the cornea. When the sensor is subjected to a change in pressure, the electrical resistance is altered and the PASCAL's computer calculates a change in pressure in accordance with the change in resistance.

The tonometer tip rests on the cornea with a constant appositional force of one gram. This is an important difference from all forms of applanation tonometry wherein the probe force is variable.

In transpalpebral diaton tonometry, a diaton tonometer is employed to measure intraocular pressure through the eyelid. It is typically regarded as a simple and safe method of ophthalmotonometry. Transpalpebral tonometry requires no contact with the cornea, therefore sterilization of the device and topical anesthetic drops are not required.

Non-contact tonometry or air-puff tonometry uses a rapid air pulse to applanate the cornea. Corneal applanation is detected via an electro-optical system. Intraocular pressure is estimated by detecting the force of the air jet at the instance of applanation.

Modern-day non-contact tonometers have been shown to correlate very well with Goldmann tonomtery measurements and have thus generally been considered a fast and simple way to screen for high IOP. Further, since non-contact tonometry is accomplished without the instrument contacting the cornea the potential for disease transmission is reduced.

Electronic indentation tonometry employs a Tono-Pen, i.e. a portable electronic, digital pen-like instrument that determines IOP by making contact with the cornea. Electronic indentation tonometry is especially useful for very young children, patients unable to reach a slit lamp due to disability, patients who are uncooperative during applanation tonometry, or patients with cornea disease in whom contact tonometry cannot be accurately performed.

In palpation tonometry, also known as digital palpation tonometry, measuring intraocular pressure is performed by gently pressing the fingertips of both index fingers onto the upper part of the bulbus through the eyelid. This technique requires medical experience and results in an estimation of the level of intraocular pressure based on the skills of the ophthalmologist.

A major drawback associated with each of the noted techniques is that each technique requires professional assistance to measure IOP.

A further drawback associated with each of the noted techniques is the need for topical anesthesia and complex instrumentation to measure IOP, which makes multiple daily measurements impractical.

It would thus be desirable to provide improved systems and methods for measuring IOP that overcome the disadvantages and drawbacks associated with conventional systems and methods for measuring IOP.

It is therefore an object of the present invention to provide systems and methods for measuring IOP that can be performed by the patient without professional assistance.

It is another object of the present invention to provide systems and methods for measuring IOP that do not require anesthesia.

It is another object of the present invention to provide systems and methods for determining outflow of aqueous humor from an eye as a function of the measured forces exerted by the eye.

SUMMARY OF THE INVENTION

In accordance with the above objects and those that will be mentioned and will become apparent below, the system for measuring IOP of an eye, in accordance with one embodiment of the invention, generally includes (i) a plurality of force sensors, the force sensors being adapted to contact a surface of an eye, (ii) means for measuring the forces exerted on the force sensors when in contact with the eye surface, and (iii) processing means, the processing means being adapted to receive the measured forces and programmed to determine intraocular pressure (IOP) of the eye as a function of the measured forces.

In one embodiment of the invention, IOP of the eye is determined by linear interpolation between two nearest IOP values by the following relationship $$p=(p_a*a+p_b*b)/(a+b) \text{ [mmHg]}$$

where:

$p_a$ and $p_b$ represent the two nearest calibration pressures, and a and b represent vertical distances to calibration curves reflecting $p_a$ and $p_b$.

In one embodiment of the invention, the processing means is further adapted to determine outflow of aqueous humor from the eye as a function of the measured forces and measured changes in IOP over time.

In one embodiment, the following pressure-volume relationship is employed by the processing means to determine the outflow of aqueous humor $$V = \frac{4\pi r_0^3}{3}\left(\frac{pr_0(1-v)}{2t_0E}+1\right)^3$$

In some embodiments of the invention, the system includes force sensor alignment means for aligning the force sensors in a desired alignment or orientation.

In one embodiment, the system includes force sensor linear transmission means that is adapted to extend and retract each of the force sensors.

In some embodiments, the force sensor linear transmission means is further adapted to secure the force sensors in desired extended and retracted positions.

In another embodiment of the invention, there is provided a method for determining intraocular pressure (IOP) of an eye, comprising the steps of: (i) providing a palpation system having first and second force sensors, the first force sensor being in a first extended position and the second force sensor being in a first retracted position with respect to the first force sensor, the first and second force sensors being adapted to contact a surface of an eye, means for measuring the forces exerted on the first and second force sensors when in contact with said eye surface, and processing means adapted to process said measured forces, (ii) placing the palpation system on a surface of the eye, whereby the extended first force sensor is in contact with the eye surface, (iii) applying a gradual first force to the eye surface with the palpation system and measuring the force exerted on the first force sensor until the retracted second force sensor contacts the eye surface, whereby the second force sensor measures a first non-zero force value, and (iv) determining IOP of the eye as a function of the force exerted on the first force sensor when the second force sensor contacts the eye surface.

In one embodiment of the invention, the method includes the step of determining IOP of the eye by linear interpolation between two nearest IOP values by the following relationship $$p=(p_a*a+p_b*b)/(a+b).$$

In one embodiment of the invention, the method includes the step of determining outflow of aqueous humor from the eye as a function of the measured forces and measured changes in IOP over time.

In one embodiment, the following pressure-volume relationship is employed to determine the outflow of aqueous humor $$V = \frac{4\pi r_0^3}{3}\left(\frac{pr_0(1-v)}{2t_0E}+1\right)^3.$$

In one embodiment, the first and second force sensors are subjected to a first palpation sequence comprising preprogrammed extension and retraction of each force sensor.

In another embodiment of the invention, the method for determining intraocular pressure (IOP) of an eye, comprises the steps of: (i) providing a palpation system having first and second force sensors, means for measuring the forces exerted on the first and second force sensors when in contact with the eye surface, and processing means adapted to process the measured forces, (ii) placing the palpation system on a surface of the eye, whereby at least one of the first and second force sensors is in contact with the eye surface, (iii) subjecting the first and second force sensors to a first palpation sequence comprising preprogrammed extension and retraction of each force sensor, (iv) measuring a first plurality of forces exerted on the first force sensor and a second plurality of forces exerted on the second force sensor over a first period of time and at a plurality of IOP values during the palpation sequence, (v) generating a plurality of calibration curves from the measured first and second plurality of forces, and (vi) determining IOP of the eye based on the generated plurality of calibration curves.

In one embodiment, IOP is determined by generating a test curve, performing a linear interpolation between the test curve and the two nearest calibration curves, and employing the following relationship:

$$p=(p_a*a+p_b*b)/(a+b).$$

In another embodiment of the invention, there is provided a the method for determining fluid displacement (i.e. outflow of aqueous humor) out of an eye, comprising the steps of: (i) providing a palpation system having first and second force sensors, means for measuring the forces exerted on the first and second force sensors when in contact with the eye surface, and processing means adapted to process the measured forces, (ii) placing the palpation system on a surface of the eye, whereby at least one of the first and second force sensors is in contact with the eye surface, (iii) subjecting the first and second force sensors to a first palpation sequence comprising preprogrammed extension and retraction of each force sensor, (iv) measuring a first plurality of forces exerted on the first force sensor and a second plurality of forces exerted on the second force sensor over a first period of time and at a plurality of IOP values during the palpation sequence, (v) generating a plurality of calibration curves from the measured first and second plurality of forces, (vi) determining IOP of the eye based on the generated plurality of calibration curves, and (vii) determining fluid displacement out of the eye as a function of the determined IOP.

In one embodiment, IOP is determined by generating a test curve, performing a linear interpolation between the test curve and the two nearest calibration curves, and employing the following relationship:

$$p=(p_a*a+p_b*b)/(a+b).$$

In one embodiment of the invention, the method of determining fluid displacement of the eye includes the step of determining the time rate of change of fluid volume in the eye as a function of IP.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 20A-20C are schematic illustrations showing one multi-probe alignment method, according to one embodiment of the invention;

FIGS. 21A and 21B are schematic illustrations showing another multi-probe alignment method for a five probe system, according to one embodiment of the invention;

DETAILED DESCRIPTION OF THE INVENTION

Figure 1:
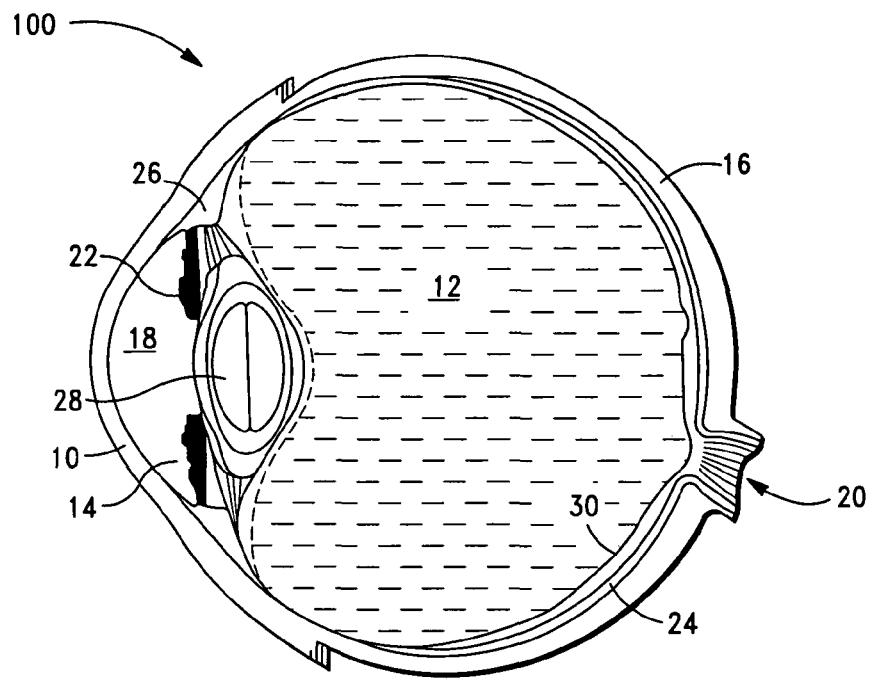
FIG. 1 is an illustration of a human eye, showing the major parts thereof.

Before describing the present invention in detail, it is to be understood that this invention is not limited to particularly exemplified methods, apparatus or systems, as such may, of course, vary. Thus, although a number of methods and systems similar or equivalent to those described herein can be used in the practice of the present invention, the preferred methods, apparatus and systems are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

As used in this specification and the appended claims, the singular forms "a", "an" and "the" include plural referents unless the content clearly dictates otherwise. As such, this statement is intended to serve as antecedent basis for use of such exclusive terminology as "solely", "only" and the like in connection with the recitation of claim elements, or use of a "negative" limitation.

Further, all publications, patents and patent applications cited herein, whether supra or infra, are hereby incorporated by reference in their entirety.

The publications discussed herein are provided solely for their disclosure prior to the filing date of the present application. Nothing herein is to be construed as an admission that the present invention is not entitled to antedate such publication(s) by virtue of prior invention. Further, the dates of publication may be different from the actual publication dates, which may need to be independently confirmed.

Definitions

The terms "probe" and "force sensor" are used interchangeably herein and mean and include a structure that is adapted to contact a surface of an eye, sense the force exerted thereon by the eye, and transmit the sensed force to an associated structure or system such as processing means.

The systems and methods for measuring intraocular pressure (IOP) and fluid discharge (i.e. outflow of aqueous humor) from an eye will now be described in detail. As will readily be appreciated by one having ordinary skill in the art, the systems and methods of the invention substantially reduce or eliminate the disadvantages and drawbacks associated with convention systems and methods for measuring characteristics associated with an eye; particularly, IOP.

As stated above and discussed in detail herein, in accordance with one embodiment of the invention, the method for measuring IOP generally comprises the steps of: (i) providing a palpation system having first and second force sensors, said first force sensor being in a first extended position and said second force sensor being in a first retracted position with respect to the first force sensor, the first and second force sensors being adapted to contact a surface of an eye, means for measuring the forces exerted on the first and second force sensors when in contact with said eye surface, and processing means adapted to process said measured forces, (ii) placing the palpation system on a surface of the eye, whereby the extended first force sensor is in contact with the eye surface, (iii) applying a gradual first force to the eye surface with the palpation system and measuring the force exerted on the first force sensor until the retracted second force sensor contacts the eye surface, whereby the second force sensor measures a first non-zero force value, and (iv) determining IOP of the eye as a function of the force exerted on the first force sensor when the second force sensor contacts the eye surface.

In another embodiment of the invention, the method for determining (IOP) of an eye, comprises the steps of: (i) providing a palpation system having first and second force sensors, means for measuring the forces exerted on the first and second force sensors when in contact with the eye surface, and processing means adapted to process the measured forces, (ii) placing the palpation system on a surface of the eye, whereby at least one of the first and second force sensors is in contact with the eye surface, (iii) subjecting the first and second force sensors to a first palpation sequence comprising preprogrammed extension and retraction of each force sensor, (iv) measuring a first plurality of forces exerted on the first force sensor and a second plurality of forces exerted on the second force sensor over a first period of time and at a plurality of IOP values during the palpation sequence, (v) generating a plurality of calibration curves from the measured first and second plurality of forces, and (vi) determining IOP of the eye based on the generated plurality of calibration curves.

As also stated above, in another embodiment of the invention, there is provided a method for determining fluid displacement (i.e. outflow of aqueous humor) out of an eye, comprising the steps of: (i) providing a palpation system having first and second force sensors, means for measuring the forces exerted on the first and second force sensors when in contact with the eye surface, and processing means adapted to process the measured forces, (ii) placing the palpation system on a surface of the eye, whereby at least one of the first and second force sensors is in contact with the eye surface, (iii) subjecting the first and second force sensors to a first palpation sequence comprising preprogrammed extension and retraction of each force sensor, (iv) measuring a first plurality of forces exerted on the first force sensor and a second plurality of forces exerted on the second force sensor over a first period of time and at a plurality of IOP values during the palpation sequence, (v) generating a plurality of calibration curves from the measured first and second plurality of forces, (vi) determining IOP of the eye based on the generated plurality of calibration curves, and (vii) determining fluid displacement out of the eye as a function of the determined IOP.

Before describing the invention in detail, the following brief description of the various anatomical features of the eye is provided, which will help in the understanding of the various features of the invention:

Since porcine eyes have been shown suitable substitutes for human eyes in IOP and glaucoma studies and, hence, are employed in the experiments and examples set forth herein, references to porcine eyes will be included in the following description of the anatomical features of an eye.

Referring to FIG. 1, the cornea 10, which is the transparent window that covers the front of the eye 100, is a lens-like structure that provides two-thirds of the focusing power of the eye. The cornea 10 is covered by an epithelium.

The cornea 10 is slightly oval, having an average diameter of about 12 mm horizontally and 11 mm vertically. The central thickness of the cornea 10 is approximately 550 µm.

The central thickness of a porcine cornea is, however, approximately 900 µm and, hence, larger than that of a human cornea.

The sclera 16 is the white region of the eye, i.e. posterior five sixths of the globe. It is the tough, avascular, outer fibrous layer of the eye that forms a protective envelope. The sclera is mostly composed of dense collagen fibrils that are irregular in size and arrangement (as opposed to the cornea). The extraocular muscles insert into the sclera behind the limbus.

The sclera 16 can be subdivided into 3 layers: the episclera, sclera proper and lamina fusca. The episclera is the most expernal layer. It is a loose connective tissue adjacent to the periorbital fat and is well vascularized.

The sclera proper, also called tenon's capsule, is the layer that gives the eye 100 its toughness. The sclera proper is avascular and composed of dense type I and III collagen.

The lamina fusca is the inner aspect of the sclera 16. It is located adjacent to the choroid and contains thin collagen fibers and pigment cells.

The pars plana is a discrete area of the sclera 16. This area is a virtually concentric ring that is located between 2 mm and 4 mm away from the cornea 10.

Figure 2A:
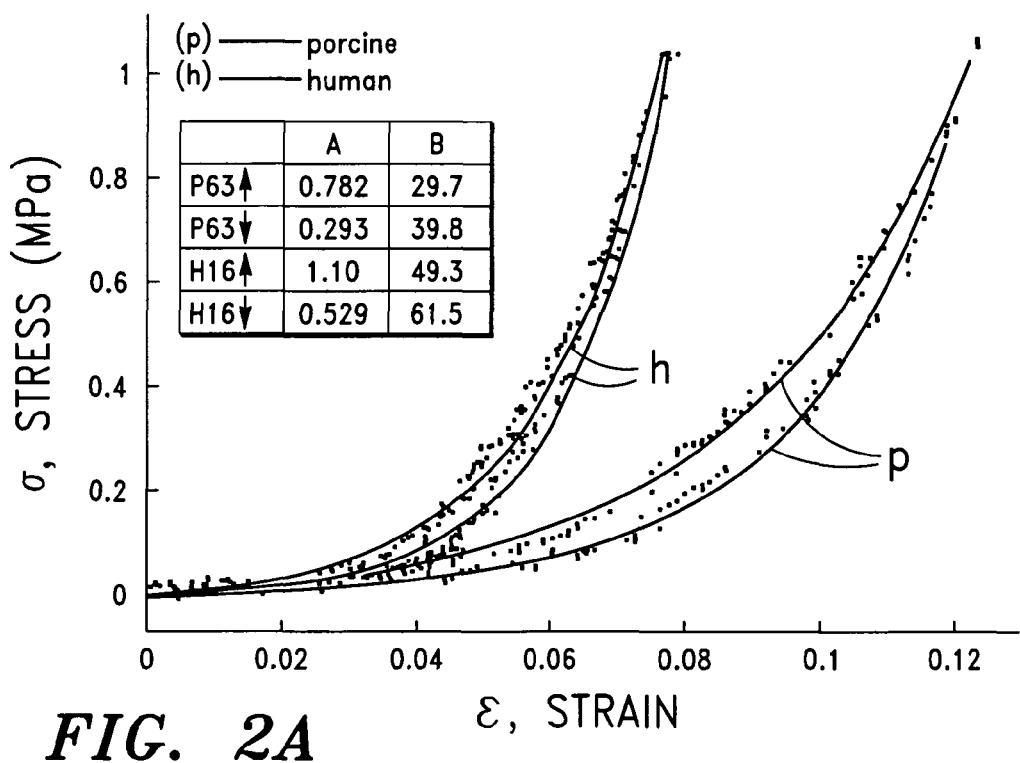
FIG. 2A is a graphical representation of the stress-strain relationship for human and porcine scleras.

As illustrated in FIG. 2A, the sclera is a hyper elastic material. According to the invention, the illustrated stress ($\sigma$)-strain ($\epsilon$) relationship of the porcine and human sclera can be described by the following relationship:

$$\sigma = A(e^{B\epsilon} - 1) \qquad \text{Eq. 1}$$

where A and B comprise material parameters.

Figure 2B:
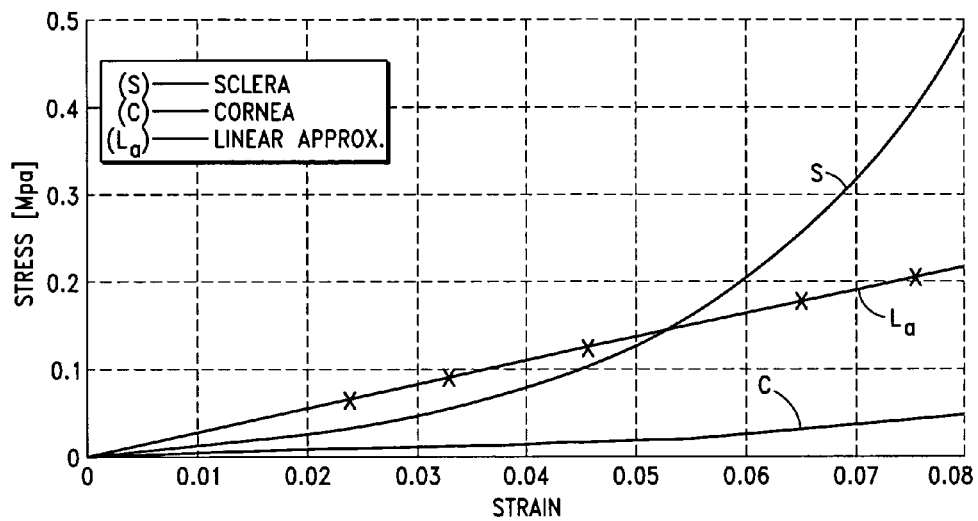
FIG. 2B is a further a graphical representation of a stress-strain relationship for a human cornea and sclera, and a linearized average stress-strain relationship therefore, according to one embodiment of the invention.

Referring now to FIG. 2B, there are shown simplified (i.e. averaged) stress-strain relationships of the sclera and cornea. FIG. 2B further shows a linear stress-strain approximation, i.e. $\sigma = E\epsilon$, which is employed in subsequent analyses herein.

Figure 3:
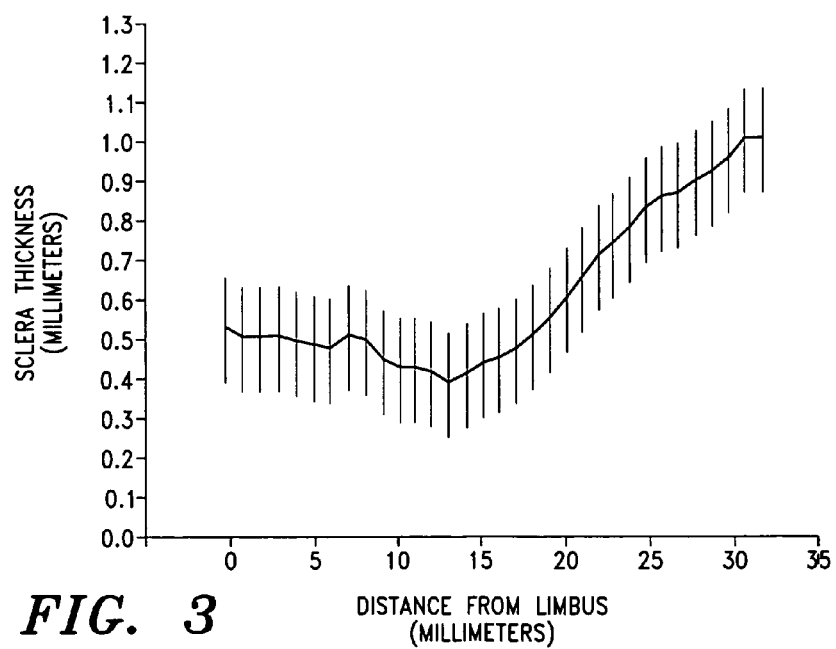
FIG. 3 is a graphical representation of the mean scleral thickness of the pars plana as a function of distance from the limbus.
Figure 4:
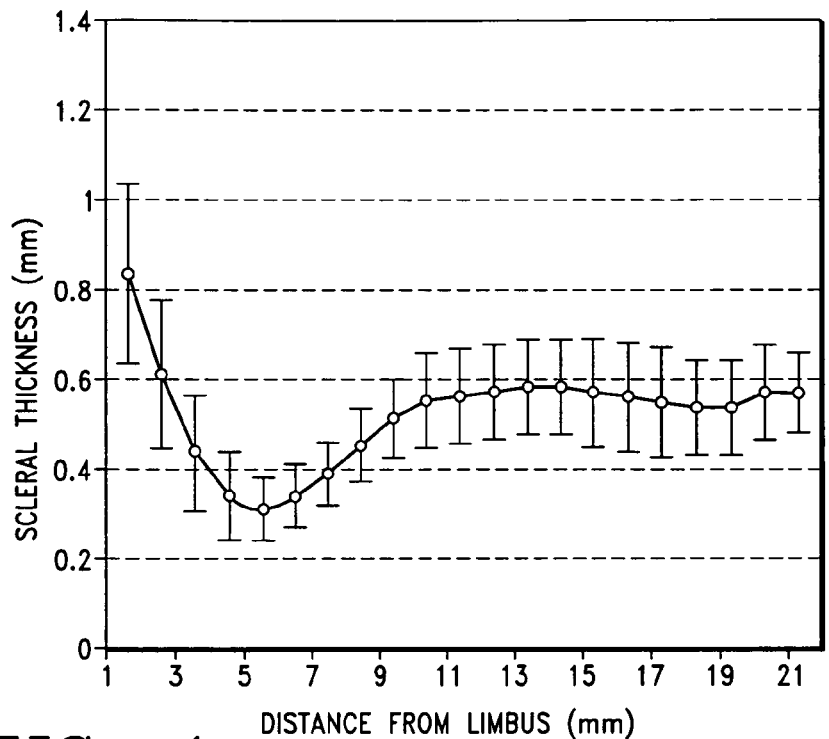
FIG. 4 is a graphical representation of mean wall thickness of a first porcine sclera as a function of distance from the limbus, illustrating the deviation thereof for a small (or light weight) porcine.
Figure 5:
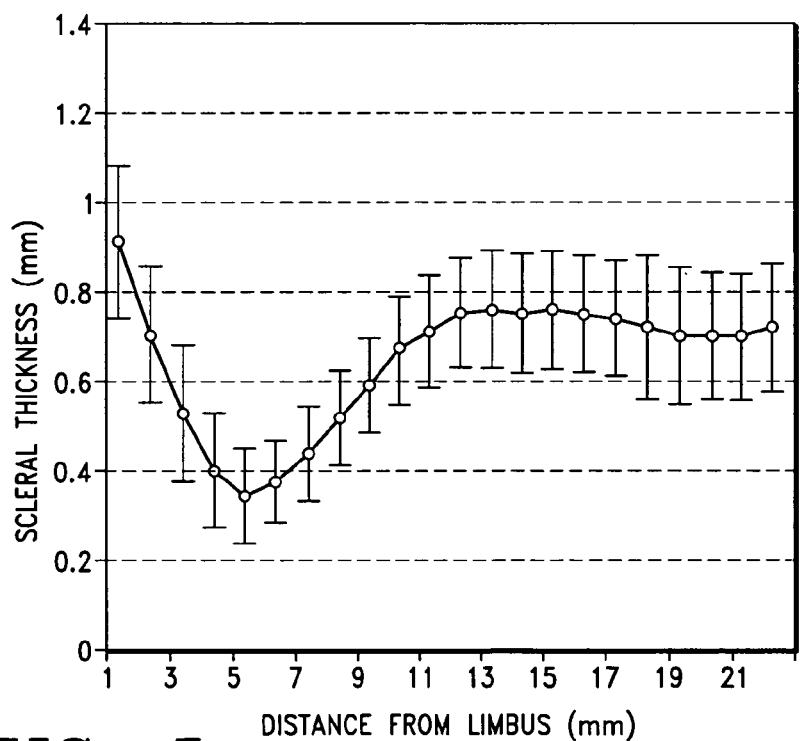
FIG. 5 is a graphical representation of mean wall thickness of a second porcine sclera as a function of distance from the limbus, illustrating the deviation thereof for a medium sized porcine.
Figure 6:
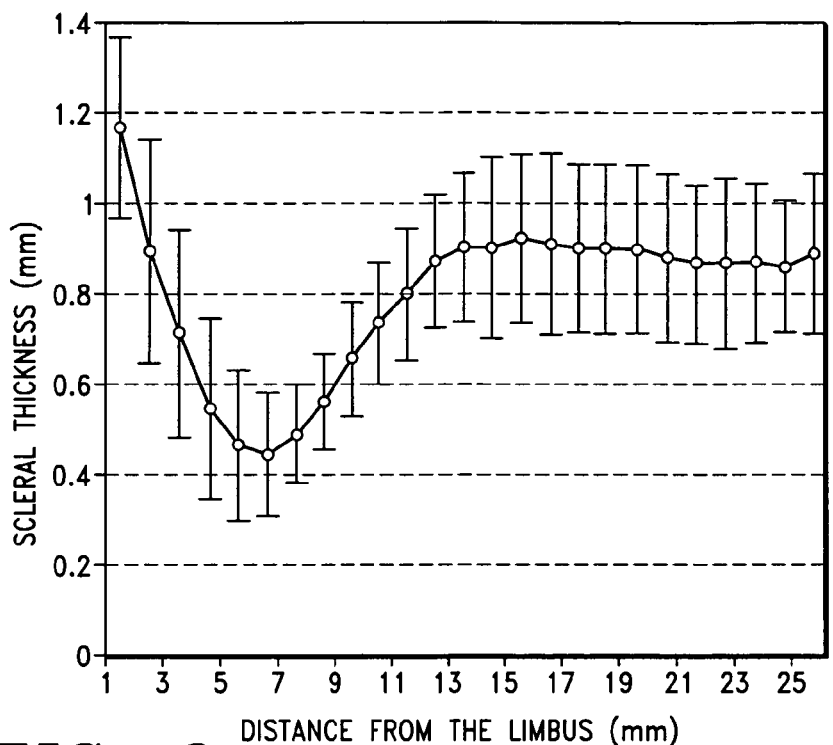
FIG. 6 is a graphical representation of mean wall thickness of a third porcine sclera as a function of distance from the limbus, illustrating the deviation thereof for a large porcine.
Figure 7:
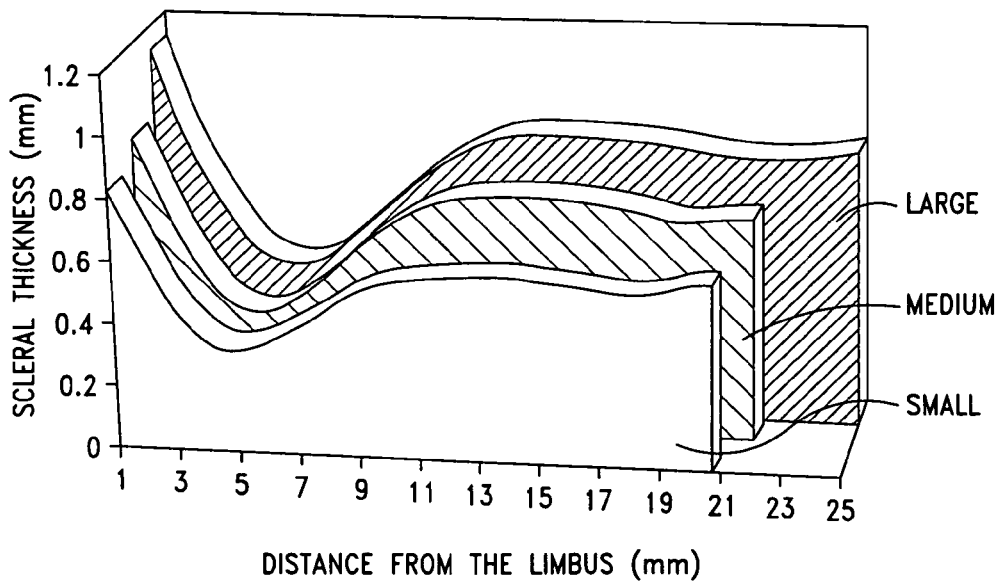
FIG. 7 is a further graphical representation showing each of the mean wall thickness characteristics of the first, second and third porcine scleras shown in FIGS. 4-6.

As illustrated in FIG. 3, the mean scleral thickness±SD of the pars plana is approximately 0.53±0.14 mm at the corneoscleral limbus, significantly decreasing to 0.39±0.17 mm near the equator, and increasing to 0.9 to 1.0 mm approximately 33 mm from the limbus, i.e. near the optic nerve 20.

The mean wall thickness of a human and porcine sclera is, however, approximately 0.75 mm. As illustrated in FIGS. 4-7, the mean wall thickness of a porcine sclera deviates substantially as a function of the weight of the porcine. Similar deviations are exhibited in the mean wall thickness of a human sclera as a function of subject weight.

The vitreous humor or vitreous 12 is the largest chamber of the eye 100 (i.e. ~4.5 ml). The vitreous 12 is a viscous transparent gel composed mostly of water. Unlike the fluid contained in the frontal parts of the eye (e.g., aqueous humor, discussed below), which are continuously replenished, the transparent gel in the vitreous chamber is stagnant.

As is well known in the art, the vitreous humor 12 also contains a random network of thin collagen fibers, mucopolysaccharides and hyaluronic acid.

The density of the vitreous humor 12 is approximately 1.0, more precisely, between approximately 1.0053 and 1.0089 g/cc.

The aqueous humor 14 occupies the anterior chamber 18 of the eye 100. The aqueous humor 14 has a volume of about 0.6 mL and provides nutrients to the cornea 10 and lens 28.

One of the most important functions of the aqueous humor 14 is to maintain the IOP by the rate of its production and drainage. The production and drainage of the aqueous humor 14 are discussed below.

The human eye produces aqueous humor at a rate of approximately 2.44 µl/min, with daytime peaks of approximately 4.26 µl/min and night time valleys of approximately 1.08 µl/min. As blood flows in the ciliary body's capillaries, it is coarsely filtered by the capillaries' endothelial cells. The resulting plasma is then refiltered by the pigmented and non pigmented ciliary epithelial cells and is secreted into the posterior chamber before traveling between the lens and iris into the anterior chamber of the eye as aqueous humor.

In accord with the Diamond-Bossert model, active transport occurring in the non pigmented ciliary epithelial cells induces small osmotic pressure gradients between the cells. A higher concentration of solutes in the proximal part of the intercellular space generates a flow of water. The concentration diminishes from the proximal part of the intercellular space to the distal part thereof, releasing the liquid into the posterior chamber.

Aqueous humor is continually produced by the ciliary processes and this rate of production must be balanced by an equal rate of aqueous humor drainage. Small variations in the changes in production or outflow of aqueous humor will have a large influence on IOP.

Figure 8:
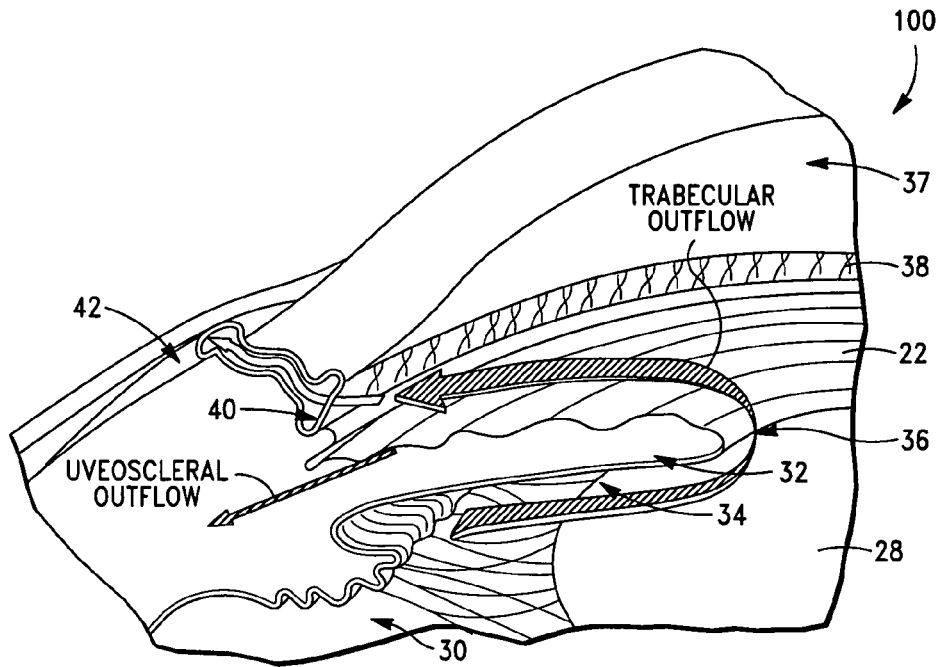
FIG. 8 is a an illustration of a portion of a human eye, showing the outflow path of aqueous humor.

As illustrated in FIG. 8, the drainage route for aqueous humor flow is first through the posterior chamber 30, then the narrow space between the posterior iris 32 and the anterior lens 34 (which contributes to small resistance), through the pupil 36 to enter the anterior chamber 37. From there, the aqueous humor exits the eye through the trabecular meshwork 38 into Schlemm's canal 40, where it flows through multiple collector canals into the episcleral veins 42.

The greatest resistance to aqueous humor flow is provided by the trabecular meshwork 38. This is where most of the aqueous humor outflow occurs.

The secondary route of aqueous humor outflow is via uveoscleral drainage, which is independent of IOP. Uveoscleral drainage occurs to a lesser extent than through the trabecular meshwork 38.

Referring back to FIG. 1, the additional parts of the eye that are illustrated therein comprise the uvea, and structures thereof, lens 28 and retina 30.

The uvea refers to the pigmented layer of the eye 100 and is made up of three distinct structures: the iris 22, ciliary body, and choroid 24. The iris 22 is the annular skirt of tissue in the anterior chamber 18 that functions as an aperture. The pupil is the central opening in the iris 22.

The ciliary body is the 6 mm portion of uvea between the iris 22 and choroid 24. The ciliary body is attached to the sclera 16 at the scleral spur. It is composed of two zones: the anterior 2 mm pars plicata, which contains the ciliary muscle 26, vessels, and processes, and the posterior 4 mm pars plana.

The ciliary muscle 26 controls accommodation (focusing) of the lens 28, while the ciliary processes suspend the lens 28 (from small fibers, i.e. zonules) and produce the aqueous humor 14 (the fluid that fills the anterior and posterior chambers and maintains intraocular pressure).

The choroid 24 is the tissue disposed between the sclera 16 and retina 30. The choroid 24 is attached to the sclera 16 at the optic nerve and scleral spur. This highly vascular tissue supplies nutrients to the retinal pigment epithelium (RPE) and outer retinal layers.

The layers of the choroid 24 (from inner to outer) include the Bruch's membrane, choriocapillaris and stroma. Bruch's membrane separates the RPE from the choroid 24 and is a permeable layer composed of the basement membrane of each, with collagen and elastic tissues in the middle.

The crystalline lens 28, located between the posterior chamber and the vitreous cavity, separates the anterior and posterior segments of the eye 100. Zonular fibers suspend the lens from the ciliary body and enable the ciliary muscle to focus the lens 28 by changing its shape.

The retina 30 is the delicate transparent light sensing inner layer of the eye 100. The retina 30 faces the vitreous and consists of two basic layers: the neural retina and retinal pigment epithelium. The neural retina is the inner layer. The retinal pigment epithelium is the outer layer that rests on Bruch's membrane and choroid 24.

Methods of modeling an eye will now be described in detail.

The mechanical model of the eyeball is based on a hyperelastic-wall sphere, which is filled with incompressible fluid. When a force or pressure is applied on the surface, the deformation of structure modifies the shape of the fluid inside.

Since a sphere has the least surface area attached to a given volume, the deformation of the original shape will increase the area of the wall (for an incompressible core), which causes meridian and tangential strains and stresses.

In order to investigate the relationship between IOP and volume, thin walled vessel equations for a pressure loaded axisymmetric membrane are employed. The equations, set forth below, facilitate the determination of the relationship(s) between meridian stress $\sigma_m$, tangential stress $\sigma_t$, radius of meridian curvature $\rho_m$, radius of tangential curvature $\rho_t$, pressure p, and wall thickness t. Equation 2 reflects the relationship between $\sigma_m$, $\rho_t$, p, and t.

$$\frac{\sigma_m}{\rho_t} = \frac{p}{2t} \qquad \text{Eq. 2}$$

now, relating the meridian stress to the strain $\epsilon$ provides $$\sigma_m = \frac{E}{1-\nu}\varepsilon. \qquad \text{Eq. 3}$$

By expressing the strain through the change of radius $$\varepsilon = \frac{r-r_0}{r_0} \qquad \text{Eq. 4}$$

where:

r represents the original radius; and $r_0$ represents the final radius a direct relationship between volume (V) and IOP (p) can be approximated by the following generalized equation $$V = V_0(\alpha p + \beta)^3 \qquad \text{Eq. 5A}$$

where:

$V_0$ represents the interior volume of the eye;

$\alpha$ is a constant and approximated by $$\alpha = \frac{r_0(1-v)}{2t_0 E}$$

and $\beta$ is also a constant.

For an idealized spherical eye model $\beta$ would be equal to 1.

According to the invention, for a simplified model of an eye, a direct relationship between volume (V) and IOP (p) can also be approximated by the following equation $$V = \frac{4\pi r_0^3}{3}\left(\frac{pr_0(1-v)}{2t_0 E} + 1\right)^3 \qquad \text{Eq. 5B}$$

The simplified models represented by Eq. 5A and 5B, above, illustrate that the volume of the intraocular fluid and IOP are related through a non-linear law.

Figure 9:
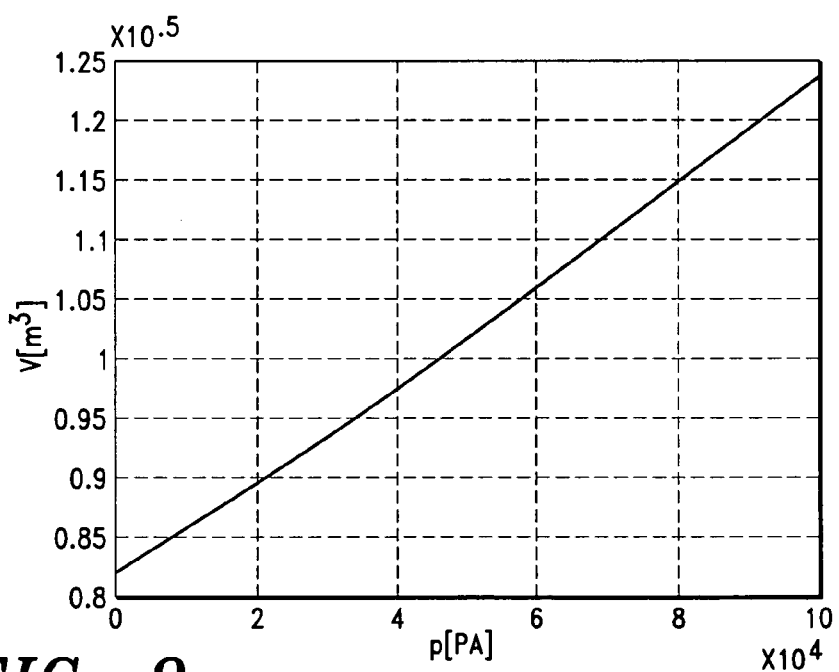
FIG. 9 is a graphical representation of the relationship between intraocular fluid volume and the intraocular pressure (IOP)

Referring now to FIG. 9, there is shown a graphical representation of the relationship between intraocular fluid volume and IOP, wherein $r_0$=12.125 mm, $t_0$=0.75 mm ($r_{outer}$=12.5 mm), E=0.5 MPa, and v=0.49. The applied pressures were 10, 15, 20, 25, 30, 35 mmHg (1 mmHg=133.33 Pa).

Equations 5A and 5B, and FIG. 9 thus demonstrate that the volume of fluid in the eye can be inferred via measurements of IOP.

Additionally, by monitoring the IOP change over a given time interval, one can deduce the amount of fluid that has been released.

This pressure-volume interdependence is the basis of one aspect of the present invention, which pertains to measuring the outflow of aqueous humor by monitoring the change in IOP over time.

The mechatronic palpation apparatus and system of the invention will now be described in detail.

As is well known in the art, a human digital palpation exam is typically performed by gently pressing the fingertips of both index fingers onto the upper part of the bulbus through the eyelid. In order to simulate this, a mechanical palpation system was designed and developed that was able to apply force to the bulbus in a number of time-varying fashions and to have control over a wide range of independent force sensor displacements.

Figure 10:
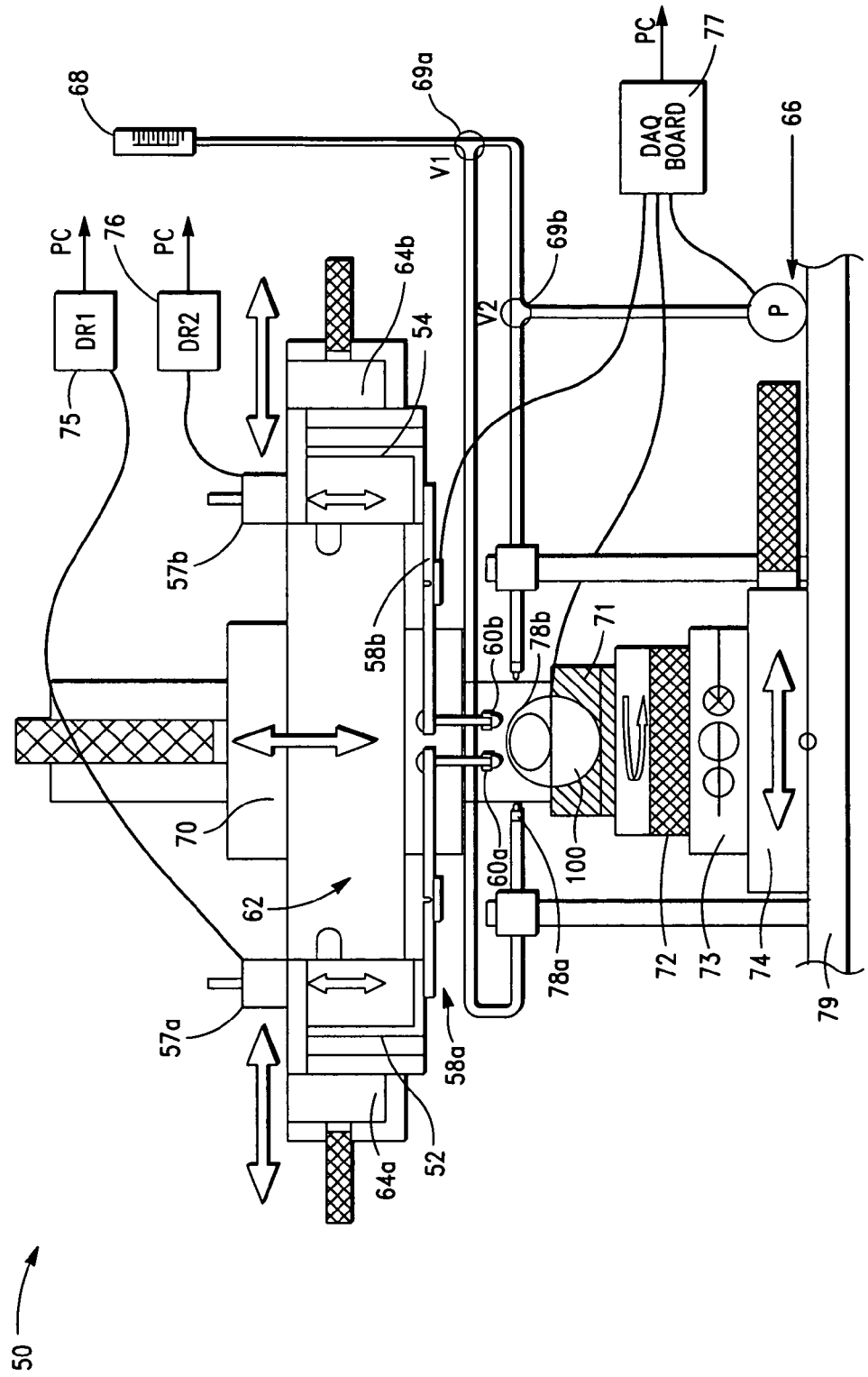
FIG. 10 is a schematic illustration of one embodiment of a mechanical palpation system, according to the invention.

Referring now to FIG. 10, there is shown one embodiment of the mechanical palpation system (denoted generally "50"), which, in the illustrated embodiment, is mounted on a base plate 79.

As illustrated in FIG. 10, the system 50 comprises two motorized linear translation stages 52, 54 that are preferably operatively connected to and controlled by a computer based position control. In a preferred embodiment, the linear translation stages 52, 54 are driven by stepper motors 57a, 57b, which, in one embodiment, are preferably adapted to provide a linear resolution of approximately 0.0254 mm (1 mill) per step.

The system 50 further includes individual force sensors 58a, 58b. As illustrated in FIG. 10, the force sensors 58a, 58b are operatively connected to each of the translation stages 52, 54. In a preferred embodiment, the force sensors 58a, 58b include probes 60a, 60b, which are adapted to contact a surface of the eye 100 and apply force thereto.

According to the invention, each of the translation stages 52, 54 is preferably attached to a common plate 62 via micrometers 64a, 64b.

In a preferred embodiment, the system 50 further includes a manual positioning stage 70, which facilitates vertical positioning via plate 62.

As illustrated in FIG. 10, the system 50 further includes a holder cup 71, which is designed and adapted to hold the eye 100 that is subject to analysis. The eye 100 is preferably positioned in the cup 71 using an aggarose gel.

The holder cup 71 is preferably attached to rotation stage 72, which is adapted and positioned to rotate the eye 100 about the vertical axis. In a preferred embodiment, the rotation stage 72 is operatively connected to linear translation stages 73 and 74, which are adapted to position the eye 100 in the horizontal plane (i.e. the plane perpendicular to the indentation direction).

The system 50 additionally includes stepper motors 57a, 57b, which are connected to electronic drivers 75, 76, respectively. The electronic drivers 75, 76 are preferably connected to and controlled by processing means, such as a personal computer (PC).

The system 50 further includes a data acquisition board 77, which is preferably designed and adapted to receive data transmitted from pressure sensor 66 and force sensors 58a and 58b. The data acquisition board 77 is preferably in communication with processing means, e.g., a PC, and is further adapted to transmit the received data thereto.

The system 50 also includes a pressure transducer 66 and a water column 68, which, as discussed below, facilitates regulation of IOP using valves 69a, 69b and needles 78a, 78b. As illustrated in FIG. 10, in a preferred embodiment, needle 78a is connected to the horizontal branch of valve 69a and a needle 78b is connected to the horizontal branch of valve 69b.

According to the invention, prior to each mechanical palpation, IOP is set by opening valve 69b to adjust the height of column 68. During mechanical palpation, valve 69b is positioned to close the connection to the water column 68, while maintaining the connection between the needle 78b and pressure transducer 66. This allows IOP to be monitored during palpation.

In a preferred embodiment, valve 69a comprises a bleeder valve that allows a small amount of fluid to replenish the fluid lost due to leakage during palpation. Prior to palpation, valve 69a is also open. However, during palpation only the vertical branch connecting valve 69a to valve 69b is closed. This allows a small amount of fluid to be bled into the eye through needle 78a and disconnects the pressure transducer 66 from the water column. In this manner, IOP can be measured through the needle 78b.

Figure 11A:
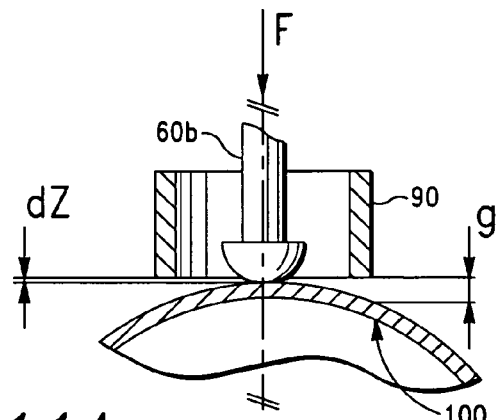
FIG. 11A is a partial sectional, schematic illustration of one embodiment of a mechanical palpation system, showing a concentric arrangement of two force probes offset from each other by a distance dZ, according to one embodiment of the invention.

Referring now to FIG. 11A, there is shown another embodiment of a mechanical palpation system of the invention. In this embodiment, probe 60a comprises a ring (denoted "90").

Figure 11B:
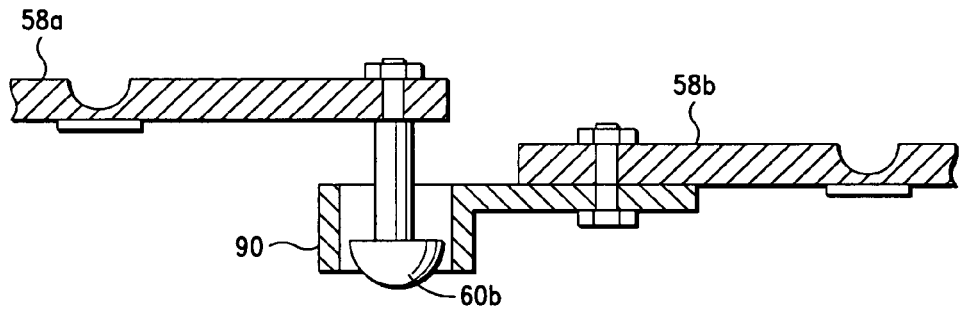
FIG. 11B is a further partial sectional illustration of the concentric arrangement of two force probes shown in FIG. 11A, according to one embodiment of the invention.

As illustrated in FIG. 11A, probe 60b is preferably disposed inside ring 90. In one embodiment of the invention, the ring 90 is connected to force sensor 58a (shown in FIG. 10) while the ring 90 is connected to the force sensor 58b (also shown in FIG. 10). This arrangement is illustrated in FIG. 11B.

In accordance with one embodiment of the invention, during mechanical palpation with the system, the tip of the extended probe 60b and the lower surface (or edge) of the retracted probe, i.e. ring 90 are preferably offset by distance "dZ".

During alignment of the probes 60b, 90 (discussed in detail below), the probe, i.e. ring 90, travels a distance "g", whereby the ring 90 is in contact with the surface of the eye 100. In one embodiment, probe 60b travels the same distance.

According to the invention, the force exerted by extended probe 60b, which is required to deform the eye surface to a desired shape, is a function of IOP, "dZ", and "g". Since "dZ" is fixed, the measured force is only a function of IOP and "g".

By aligning the probes of the invention, e.g., probes 60b, 90, with respect to the eye 100, as discussed below, the variation of "g" can be eliminated, whereby the force measured by probe 60b is only a function of the IOP.

Figure 12:
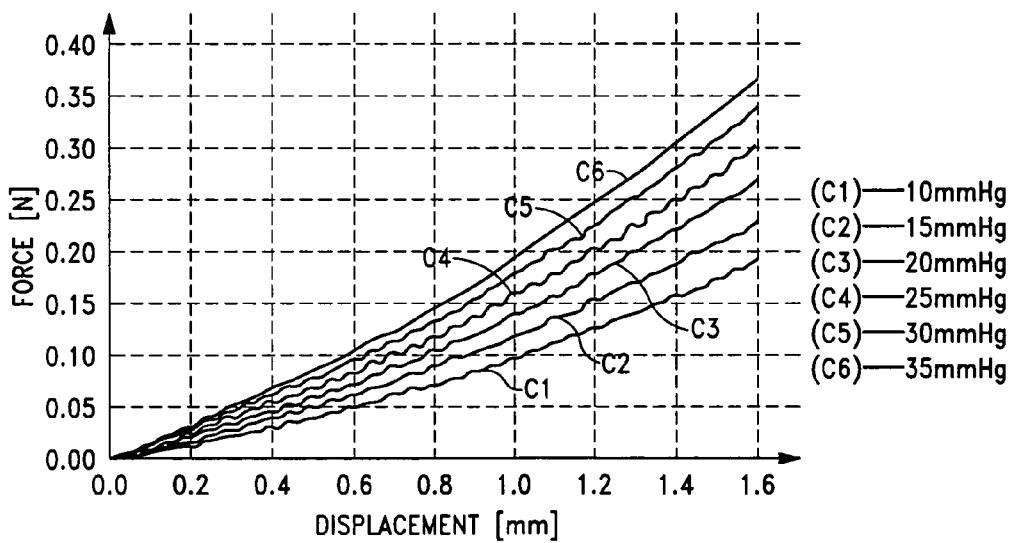
FIG. 12 is a graphical representation of the relationship between indentation force applied by a probe of the invention and displacement for different values of IOP, according to one embodiment of the invention.

Referring first to FIG. 12, there is shown a graphical illustration of force versus displacement of an eye with different values of IOP, where only one probe, such as probe 60b, was employed to exert the force. As demonstrated in FIG. 12, the stiffness of the eye (represented by the slope of the curves) increases with higher values of IOP.

FIG. 12 further establishes that IOP can be inferred (or determined) from the slope of the curves reflecting the relationship between force and displacement. The inferred IOP does, however, require force and displacement measurement of the probe with respect to the eye.

To eliminate the need to measure the displacement of the probe, the palpation systems of the invention employ multiple probes. According to the invention, any number of probes can be employed within the scope of the invention. In one embodiment of the invention, discussed in detail below, the system includes two probes (or force sensors).

Figure 13A:
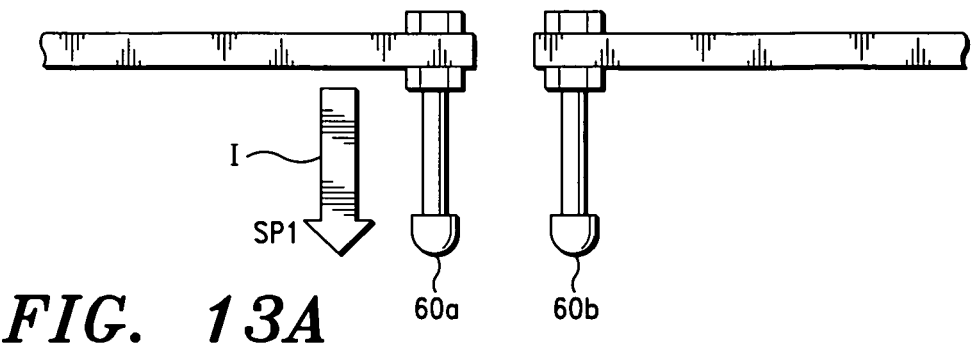
FIGS. 13A-13D are schematic illustrations of one embodiment of a mechanical palpation system having first and second force probes, showing a palpation with the two probes, according to one embodiment of the invention.
Figure 13B:
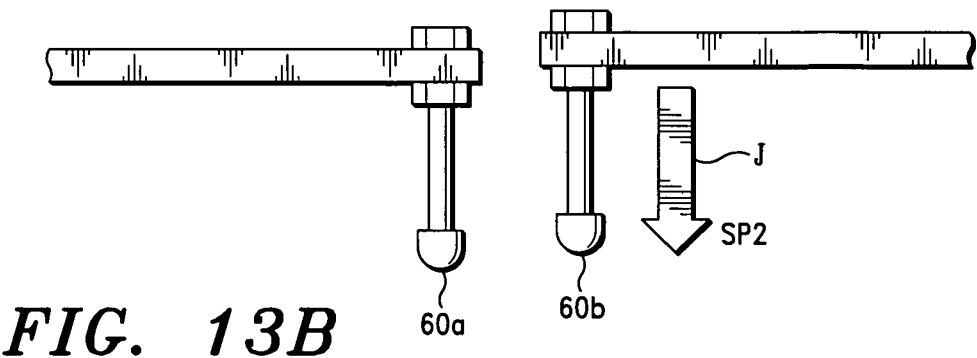

Referring now to FIGS. 13A-13D, there is shown a sequence of palpation with two probes 60a, 60b, according to one embodiment of the invention. Referring first to FIG. 13A, according to the invention, probe 60a is initially advanced a fixed distance (i.e. set point denoted "SP1") in the direction of arrow I. The second probe, i.e. probe 60b is then advanced a distance slightly less than probe 60a (i.e. to set point denoted "SP2") in the direction of arrow J, as shown in FIG. 13B.

Figure 13C:
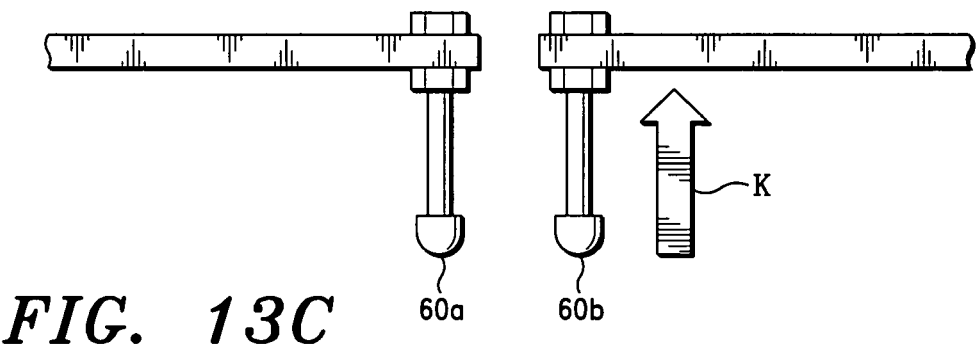
Figure 13D:
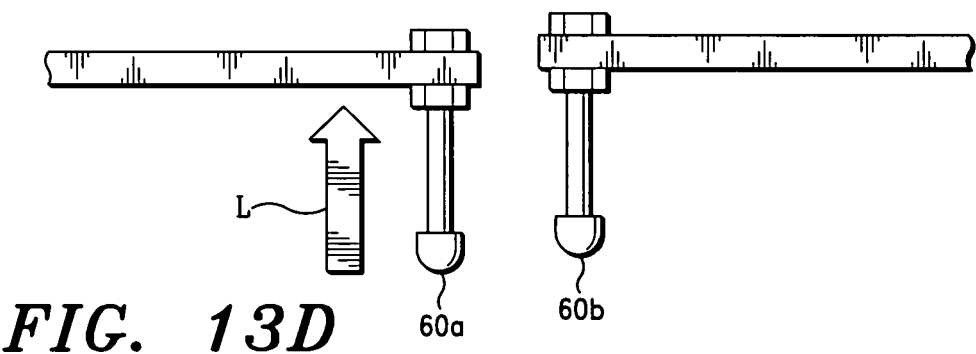

Subsequently, probe 60b is retracted in the direction of arrow K, as shown in FIG. 13C. Thereafter, probe 60a is retracted in the direction of arrow L.

Figure 14:
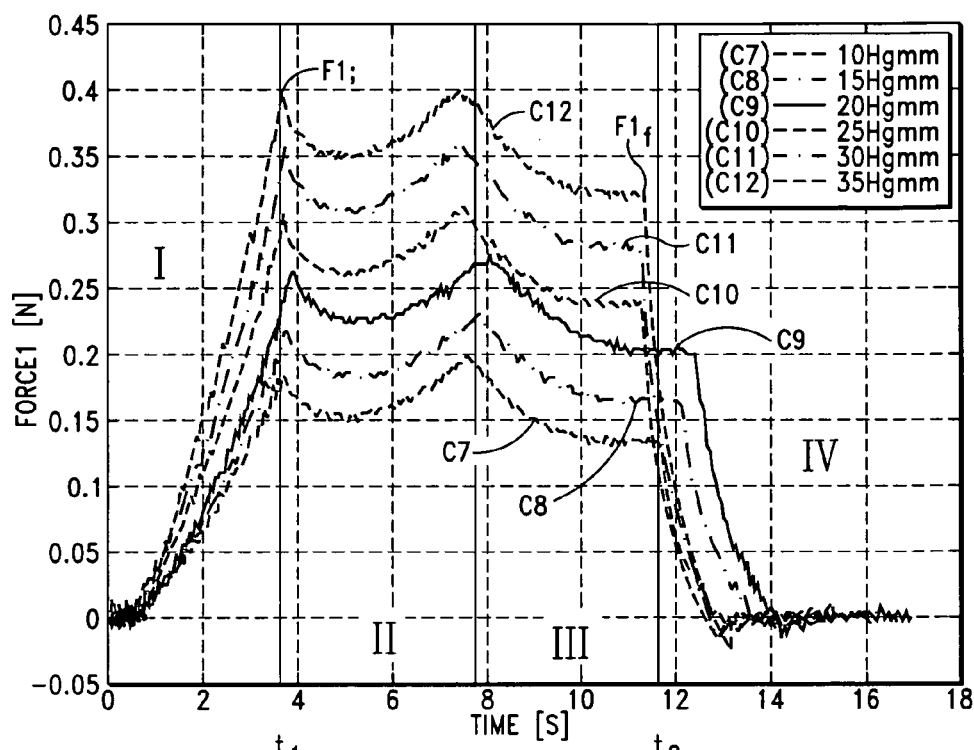
FIG. 14 is a graphical representation of the forces measured by the first probe shown in FIGS. 13A-13D during the palpation sequence illustrated in FIGS. 13A-13D, according to one embodiment of the invention.
Figure 15:
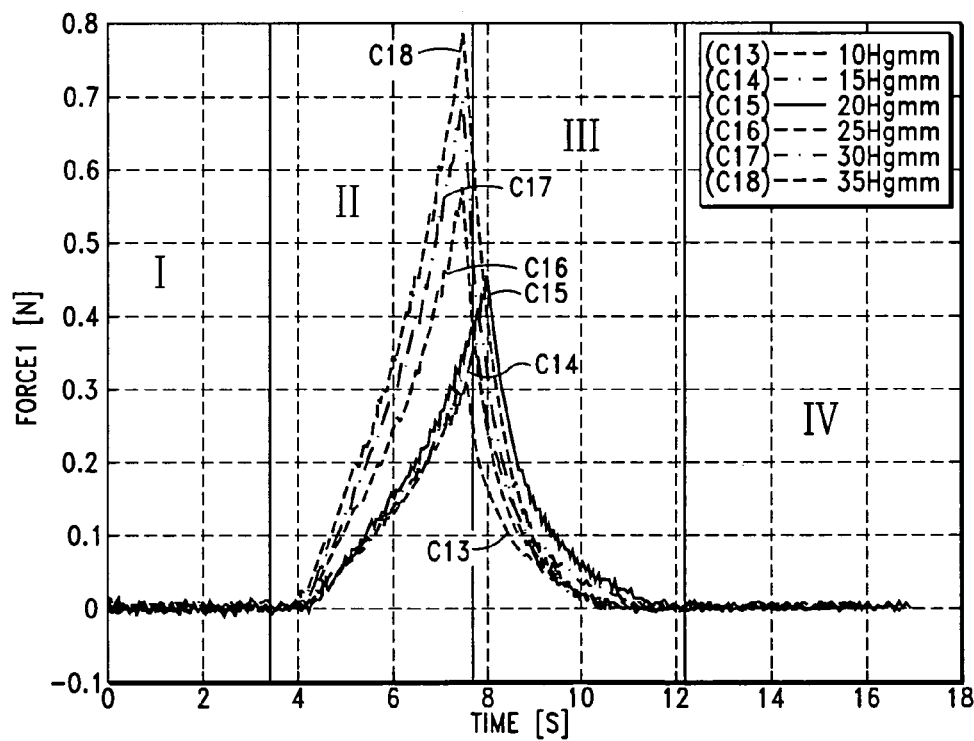
FIG. 15 is a graphical representation is the forces measured by the second probe shown in FIGS. 13A-13D during the palpation sequence illustrated in FIGS. 13A-13D, according to one embodiment of the invention.

Referring now to FIGS. 14 and 15 there is shown a graphical representation of the relationship between measured forces and time (at various IOP values) for probes 60a, 60b, respectively, during the palpation sequence illustrated in FIGS. 13A-13D. Regions I-IV shown in FIGS. 14 and 15 represent the four palpation steps illustrated in FIGS. 13A-13D.

FIGS. 14 and 15 demonstrate that the relationship between measured force and time is strongly dependent on IOP, as evident by the shifts in curves C7-C12 (FIG. 14) and curves C13-C18 (FIG. 15) toward higher forces with elevated IOP.

Figure 16:
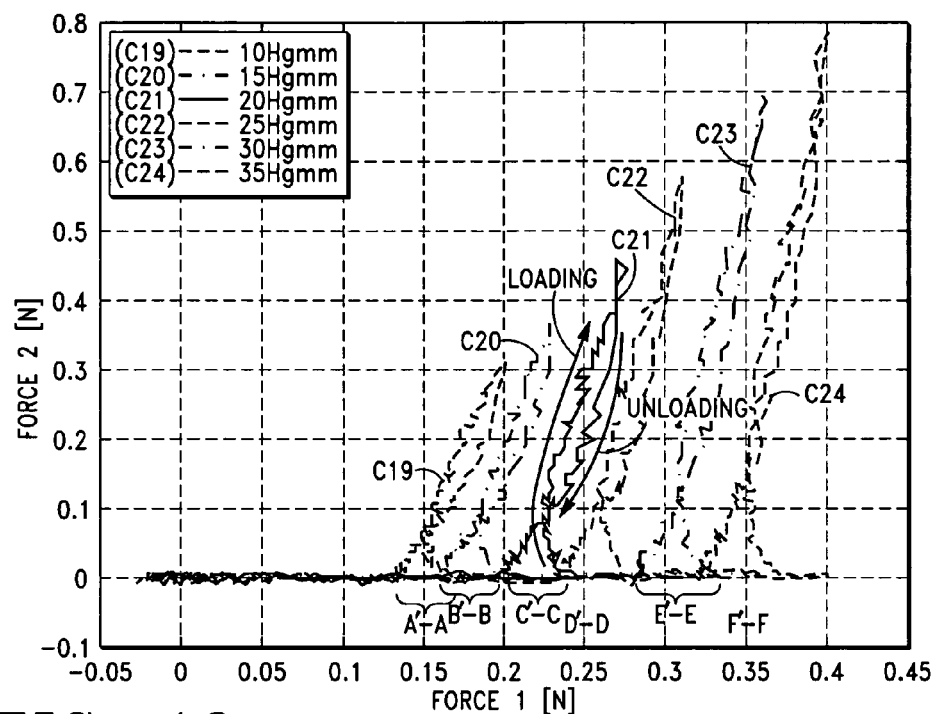
FIG. 16 is a graphical representation of superpositioned forces measured by the first probe (horizontal axis) and second probe (vertical axis) shown in FIGS. 13A-13D during the palpation sequence illustrated in FIGS. 13A-13D, according to one embodiment of the invention.

When the data from probe 60a is plotted against the data from probe 60b (i.e. the time and displacement information is omitted), one obtains the graphical representation shown in FIG. 16, i.e. force 1 (probe 60a) versus force 2 (probe 60b). The period identified as "Loading" represents the forward motion of probe 60b, while the period labeled "Unloading" represents the retraction of the probe 60b.

As illustrated in FIG. 16, each of the curves, i.e. curves C19-C24, has a characteristic loop, i.e. hysteresis loop, which is formed during the advancement and retraction of the probes. The noted hysteresis results from an increase in IOP during the advancement and retraction of the probes and the proximity (and effect thereby) of the two probes 60a, 60b. Initially, advancement of probe 60b deforms the eye surface near probe 60a and relieves some of the force measured by probe 60a. Further advancement of the probe 60b raises the IOP and correspondingly the force exerted on (and, hence, measured by) probe 60a. During "unloading" (retraction of probe 60b), the force measured by probe 60a diminishes monotonically, but does not retrace the loading curve.

The change in the path between the loading and unloading curves represents the loss of intraocular fluid during this elevated IOP period. This is represented by the difference in the force measured by probe 60a at the beginning of the loading cycle (point C on curve C21) and the end of this period (point C' on curve C21). A similar effect is observed for each of the test pressures represented by curves C19-C24) (i.e. points A-A' on curve C19, points B-B' on curve C20, points D-D' on C22, and points E-E' on C23).

FIG. 16 thus demonstrates that displacement measurements of individual probes are not necessary; provided, the probes move at a fixed distance with respect of each other. Under such conditions, each force versus time curve, such as the curves C7-C12 and C13-C18 shown in FIGS. 14 and 15, is clearly separated from the rest for different values of IOP.

Consequently, IOP can be measured by using two probes that are offset a fixed distance from each other, for example, by having one probe in an extended position and the other at a retracted position. The extended/retracted arrangement is illustrated in FIG. 11, where one of the probes, i.e. probe 90, comprises a ring.

Figure 17:
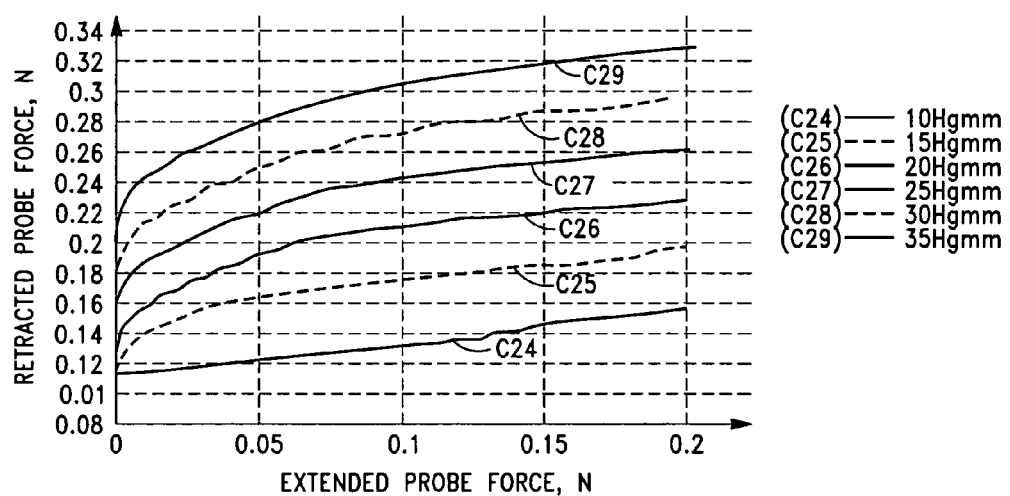
FIG. 17 is a graphical representation of measured forces exerted on an extended and retracted probe by an eye (at different IOP values) during simultaneous movement of the probes (i.e. calibration curves), where the horizontal axis represents the force exerted on the extended probe and the vertical axis represents the force on the retracted probe, according to one embodiment of the invention.

Referring now to FIG. 17, there is shown a graphical representation of measured forces exerted on extended and retracted probes (at different IOP values) during simultaneous movement of the probes, where the horizontal axis represents the force exerted on the extended probe (denoted "N"') and the vertical axis represents the force on the retracted probe (denoted "N"). As illustrated in FIG. 17, each value of IOP results in a separate calibration curve, i.e. curves C24-C29.

According to the invention, one method of extracting IOP from the data reflected in FIG. 17, is to generate a test curve and compare it with a set of calibration curves. This is illustrated in FIG. 18, where C30 denotes the test curve and C24-C29 denote the calibration curves shown in FIG. 17.

Figure 18:
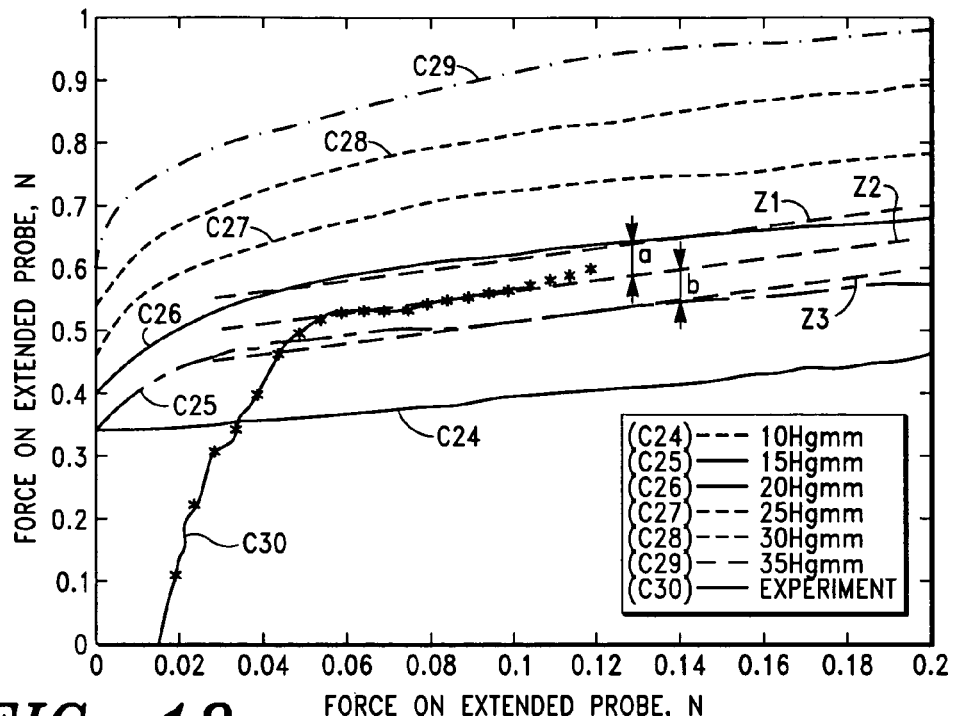
FIG. 18 is a further graphical representation of measured forces exerted on an extended and retracted probe by an eye superimposed over the calibration curves shown in FIG. 17, where the distances a and b represent the distances to the nearest calibration curves, according to one embodiment of the invention.

According to the invention, by fitting a line ("Z2") through the flat portion of experimental curve C30 and the two lines ("Z1" and "Z3") through the flat portions of the nearest calibration curves, i.e. curves C25 and C26, as shown in FIG. 18, distances a and b can be determined.

According to the invention, IOP (p) can then be determined by linear interpolation between the two nearest IOP values by the following relationship:

$$p=(p_a*a+p_b*b)/(a+b) \text{ [mmHg]} \qquad \text{Eq. 6}$$

where $p_a$ and $p_b$ are the two nearest calibration pressures and a and b are the vertical distances to the calibration curves reflecting the pressures (as described above).

As indicated above and reflected in FIG. 16, applicants have further found that during mechanical palpation, the force values obtained during advanced of the probes does not coincide with the force values obtained during the retraction, i.e. a small amount of hysteresis exists. The noted hysteresis is caused, in significant part, from leakage (i.e. loss) of intraocular fluid during palpation.

As reflected by Eqs. 5A and 5B, above, IOP is directly related to the volume of the incompressible fluid occupying the eye. Therefore, measuring the amount of IOP reduction during palpation can be correlated with the amount of fluid that has been lost.

The pressure-volume relationship expressed in Eq. 5B can thus be used to extract a numerical estimate of the amount of fluid discharged out of the eye (i.e. outflow of aqueous humor).

According to the invention, if $\dot{V}$ is the time rate of change of fluid volume in the eye, one can differentiate Eq. 5B with respect to time to obtain $\dot{V}$ $$\dot{V}=3\alpha V_0(\alpha p+1)^2 \dot{p} \quad \text{Eq. 7}$$

where:

$$V_0 = 4\pi r_0^3/3; \text{ and}$$

$$\alpha = \frac{r_0(1-\nu)}{2t_0 E}.$$

For short periods of time, i.e. the duration of the IOP measurement, Eq. 7 can be re-written in a differential form to show the time dependence of volume change versus pressure change, i.e.

$$\Delta V=3\alpha V_0(\alpha p+1)^2 \Delta p \quad \text{Eq. 8}$$

Equation 8, above, shows that the pressure drop $\Delta p$ is proportional to the change of volume of the intraocular fluid $\Delta V$.

As is well known in the art, one treatment of glaucoma involves placement of drainage shunt implants that are designed to release some of the aqueous humor produced by the eye. Therefore, the method described herein and illustrated by Eq. 8 shows that measuring pressure drop over short time intervals can be can be used to monitor the amount of fluid that has been drained through natural and man-made leakage paths, such as the glaucoma drainage implants.

Figure 19:
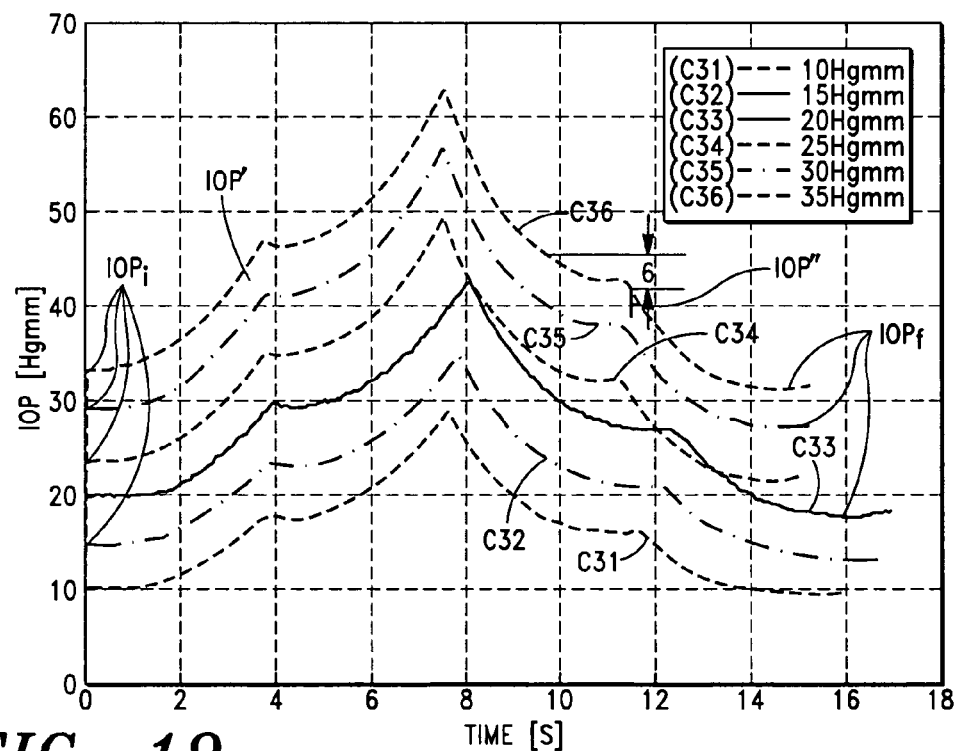
FIG. 19 is a graphical representation of the relationship between IOP and time after the palpation sequence illustrated in FIGS. 13A-13D, according to one embodiment of the invention.

Referring now to FIG. 19, there is shown a graphical illustration of variations in IOP as a function of time, during mechanical palpation. As illustrated in FIG. 19, the final IOP (denoted "IOP$_f$" @ time=~15 sec.) is typically lower than the initial IOP (denoted "IOP$_i$" @ time=0).

However, the values "IOP$_i$" and "IOP$_f$" reflected in FIG. 19 are not available as direct measurements. According to the present invention, the decrease of IOP is also detectable with force measurements in the form of shift (i.e. hysteresis) between the curves obtained during advancement and retraction of the force probes. This is shown in FIG. 16, where the distances (shift) between the curves is denoted by distances A'-A, B'-B, C'-C, D'-D, E'-E, and F'-F.

Thus, by applying a programmed mechanical pressure or force to the eye, it is possible to discern the amount of fluid that has escaped from the eye from the shift(s) of the force curves obtained from employing the probes of the invention.

By the term "programmed mechanical force and pressure", as used herein, it means that the force is applied in controllable or measurable manner. For example, one can use the weight of a probe for a given amount of time and monitor the change of force on individual probes, or can record the values of forces over time and use a time-integral (the average force) to determine the time between the two force measurements.

The methods of the invention described herein thus include the step of applying a predetermined and/or preprogrammed force (or forces) to the eye via a plurality of probes.

Figure 23:
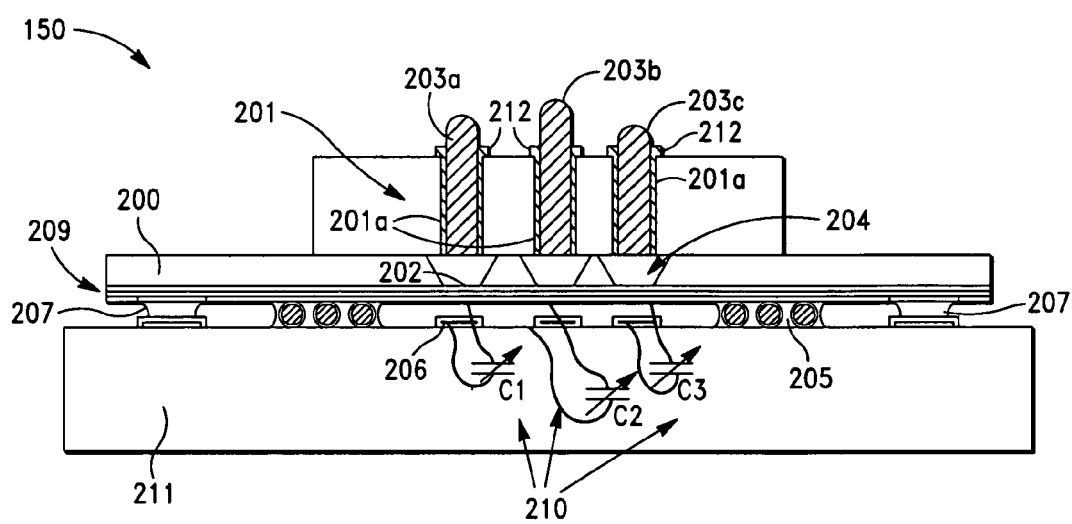
FIG. 23 is a schematic illustration of another embodiment of a palpation system, according to the invention.

Referring now to FIG. 23, there is shown yet another embodiment of a palpation system of the invention (denoted "150"), having three probes or pins 203a, 203b, 203c. As illustrated in FIG. 23, each of the probes 203a, 203b, 203c preferably has a different length.

The pins 203a, 203B, 203c are preferably housed in a block 201, having three lumens 201a that are adapted to receive and guide the pins 203a, 203b, 203c and prevent an overload. The block 201 is preferably operatively connected to a MEMS sensor chip 200 containing etched cavities 204.

Each of the pins 203a, 203b, 303c preferably contain a rim 212, which serves the function of preventing mechanical overload.

In one embodiment, the bottom of the MEMS sensor chip 200 includes a thin layer 209, which forms flexible diaphragms 202 at the base of each cavity 204. In one embodiment, the cavities are filled with an adhesive, such as polydimethylsiloxane (PDMS), which serves the function of transmitting the force exerted on the pins 203a, 203b, 203c to the diaphragms 202.

In one embodiment of the invention, the force is determined as a function of the deflection of the diaphragms 202. In one embodiment, the deflection of the diaphragms 202 is determined via capacitance measurement(s).

In the noted embodiment, layer 209 comprises a conductive film having an array of capacitors 210 disposed proximate the base of each cavity 204. Three counter electrodes 206 are also included, which are preferably disposed on dielectric substrate 211 in substantial alignment with the base of each cavity 204.

In another embodiment of the invention, the deflection of the diaphragms 202 is determined using piezoresistive strain gauges diffused into layer 209.

According to the invention, electrical connections between substrate 211 and the MEMS sensor chip 200 are facilitated via bonding pads 207.

In some embodiments of the invention, mechanical spacers 205, comprising glass beads mixed with adhesive, are used to provide uniform separation between the substrate 211 and the MEMS sensor chip 200.

A key advantage of the system 150 illustrated in FIG. 23, as well as system 50 shown in FIG. 10, is that the systems 150, 50 can be readily integrated into a hand held palpation unit.

In order to achieve the desired force(s) on an eye with multiple probes, it is preferred that the probes are aligned with respect to the surface of the eye. According to the invention, two methods can be employed to align the probes. Each of the methods is discussed below.

In the first probe alignment method, additional force probes, i.e. more than two, are employed. According to the invention, any number of probes can be employed, e.g., 3, 5, etc.

In one embodiment of the invention, illustrated in FIGS. 20A-20C, three (3) probes are employed. According to the invention, probe misalignment can be detected by the difference in the values of forces measured by the outer two probes—denoted "L" (for the left probe) and "R" (for the right probe), respectively; "C" representing the center probe.

FIG. 20A illustrates optimal probe alignment, wherein the values of forces measured by the outer two probes L and C are equal. FIGS. 20B and 20C illustrate probe misalignment, wherein the values of forces measured by the outer two probes L and C are not equal.

Referring now to FIGS. 21A and 21B, there is shown a further illustration of a probe configuration, according to one embodiment of the invention. As illustrated in FIGS. 21A and 21B, five probes, denoted 110, 112, 114, 116, 118 are employed.

In the illustrated embodiment, the four outer probes, i.e. probes 110-116, are used to ascertain proper alignment, for example, by verifying that the forces associated with each probe are equal.

As will readily be appreciated by one having ordinary skill in the art, the noted probe configuration facilitates alignment in multiple planes; FIG. 21B illustrating alignment in plane $P_x$ via the observed forces of probes 110, 114, and 116.

In practice, the user may tilt the unit until the probes are appropriately aligned. The measurement will then record the value of all five force probes, i.e. probes 110, 112, 114, 116, 118, and proceed with the determination of the IOP, as described earlier.

According to the invention, a system with three alignment and at least one extended or retracted probes is also possible.

According to the invention, the five probe arrangement can also comprise at least three alignment probes and at least one extended or retracted probe. In the noted arrangement, probe alignment is achieved by verifying that the forces measured by the alignment probes are either equal, or satisfy a predetermined condition. For example, if the surface curvature is not uniform, it might be desirable that some of the forces measured by the alignment probes are lower (or greater) than the rest to accommodate the unevenness of the eye surface. To aid in the alignment, the user might be provided with audible or visual cues, for example, by using a variable pitch tone, or a graphical display indicating the degree of force imbalance.

Figure 22:
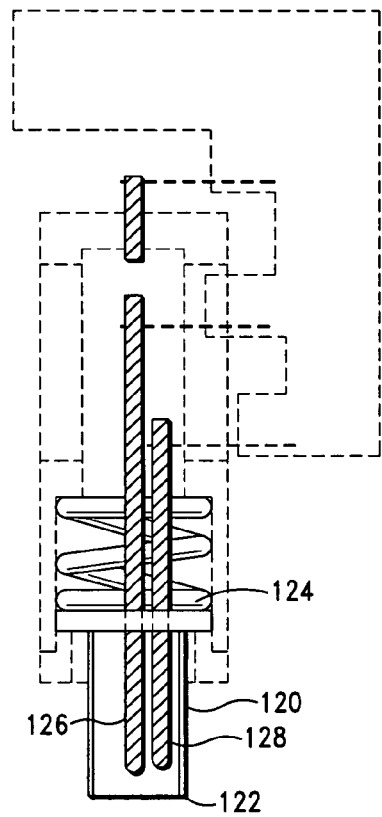
FIG. 22 is a schematic illustration showing another probe alignment method, where the probe includes a self-aligning mechanism, according to one embodiment of the invention.

The second probe alignment method employs a surface that conforms to the contour of the eye and relies on self-alignment. According to the invention, the conforming surface can comprise various system structures and/or portions thereof. For example, the conforming surface can comprise the outer arced surface of a probe. In one embodiment of the invention, illustrated in FIG. 22, the conforming surface comprises the outer edge 122 of a tubular probe 120.

In some embodiments of the invention, a spring 124 is included that allows the aligning structure to retract and expose the measuring force probes (denoted 126, 128, respectively).

EXAMPLES

The following examples are given to enable those skilled in the art to more clearly understand and practice the present invention. They should not be considered as limiting the scope of the invention, but merely as being illustrated as representative thereof.

Example 1

Measurement of IOP

As discussed in detail above, IOP can be determined by linear interpolation between the two nearest IOP values by the following relationship:

$$p=(p_a*a+p_b*b)/(a+b) \text{ [mmHg]}$$

where $p_a$ and $p_b$ are the two nearest calibration pressures and a and b are the vertical distances to the calibration curves reflecting the calibration pressures, i.e. $p_a$ and $p_b$.

By way of example, from experimental curve C30 shown in FIG. 18, the distance to the two nearest calibration curves is a=0.04 N and b=0.05 N. The two nearest calibration pressures are $p_a$=20 mmHg and $p_b$=15 mmHg, respectively.

Using Eq. 6, shown above, IOP (p) is determined as follows:

$$p=(0.04\times 20+0.05\times 20)/(0.04+0.05)=17.22 \text{ mmHg}.$$

Example 2

Measurement of Fluid Discharge, i.e. Aqueous Humor Outflow, from an Eye

In the following example Equations 8 and 14, and FIG. 19, above, are employed.

As discussed above and illustrated by Eq. 8, fluid outflow from an eye is proportional to the change of IOP over a given time interval. During mechanical palpation with one or more probes, the IOP inside the eye increases as a result of application of external force. A finite fluid resistance and increased IOP leads to an increase in the outflow from the eye.

Upon removal of an external force, IOP generally returns to a value that is lower than its initial value. This phenomenon is shown in FIG. 19, i.e. curves C31-C36, where each of these curves represents a separate palpation sequence, as illustrated in FIGS. 13A-13D. As discussed above and illustrated below, the amount of fluid discharge or outflow from an eye can be determined (or estimated) from the data embodied in each of the curves, i.e. curves C31-C36, shown in FIG. 19.

For example, from FIG. 19, curve C36 reflects an initial IOP value ($IOP_i$) equal to approx. 46.5 mmHg and a final IOP value ($IOP_f$) equal to approx. 42.5 mmHg. From FIG. 14, $\Delta p$=46.5−42.5=4.0 mmHg=4*133=532 Pa Using the following parameters: $r_0$=12.5 mm, $t_0$=0.8 mm, E=2.7 MPa and Poisson ratio (ν)=0.495, the interior volume of the eye ($V_0$) can be determined as follows:

$$\alpha = \frac{r_0(1-v)}{2t_0 E} = \frac{12.5E-3\times(1-0.495)}{2\times 0.8E-3\times 2.7\times 10^6} = 1.461E-6, \text{Pa}^{-1}$$

$$V_0 = 4\pi r_0^3/3 = 8182 \text{ μL}$$

From FIG. 19, the average pressure between $IOP_i$ and $IOP_f$ (denoted IOP' and IOP") on curve C36 is as follows: p=49.8 mm Hg=49.8*133=6623 Pa.

Using Eq. 8, the fluid outflow from the eye (ΔV) can be determined as follows:

$$\Delta V=3\alpha V_0(\alpha p+1)^2 \Delta p=16.31 \text{ μL}.$$

The fluid outflow from the eye during the period between IOP' and IOP", i.e. 7.7 seconds, is thus 16.31 μL. The average outflow rate is thus 16.31/7.7=2.12 μL/s.

Example 3

Measurement of Aqueous Humor Outflow From an Eye

In this example, instead of using the curves shown in FIG. 19, i.e. curves C31-C36, the force curves shown in FIG. 14, i.e. curves C8-12, are employed. As illustrated in FIG. 14, curves C8-12 reflect measured initial and final force values, $F1_i$ and $F1_f$, at $t_1$ and $t_2$, respectively, measured with a first probe during palpation with a second probe.

Fluid outflow from the eye can then be determined from the following relationship $$\Delta V=K(F1_i-F1_f)$$

From curve C12 in FIG. 14 (i.e. p=35 Hgmm), $F1_i$=approx. 0.404 N and $F1_f$=approx. 0.32 N, therefore $$K = \frac{\Delta V}{F1_i - F1_f} = \frac{16.31}{0.404 = 0.32} = 194.2 \text{ μL/N}.$$

As will readily be appreciated by one having ordinary skill in the art, the present invention provides numerous advantages over conventional systems and methods for measuring IOP. Among the advantages are the following:

The provision of IOP measuring systems and methods that facilitate measurement of IOP by a patient without professional assistance.

The provision of IOP measuring systems and methods that facilitate measurement of IOP that do not require numbing medications.

The provision of IOP measuring systems and methods that facilitate measurement of aqueous humor outflow through its natural outflow path or through implanted drainage shunts.

The provision of IOP measuring systems and methods that utilize a miniaturized, and integrated multi-force sensor based on MEMS technology.

The invention also demonstrates that volume of fluid in an eye can be inferred via IOP measurements, and by monitoring IOP change over a given time interval, one can deduce the amount of fluid that has been discharged from the eye.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A system for measuring intraocular pressure (IOP) of an eye, comprising:
   a plurality of force sensors, said force sensors being adapted to contact a surface of an eye structure;
   means for measuring forces exerted on said force sensors when said force sensors are in contact with said eye structure surface;
   control means in communication with said force measuring means for controlling said plurality of force sensors, said control means including programming means adapted to control forces transmitted to said eye structure surface by said force sensors when said force sensors are in contact with said eye structure surface, said control means further including sensor orientation means for determining a first measurement condition, said first measurement condition being determined as a function of a first plurality of forces measured by said sensors when said force sensors are in contact with said eye structure surface,
   said control means being further adapted to acquire a second plurality of forces measured by said sensors when said first measurement condition is determined,
   said control means additionally including processing means for processing said measured second plurality of forces, said processing means being adapted to receive said second plurality of measured forces and programmed to determine intraocular pressure (IOP) of the eye as a function of said second plurality of measured forces.

2. A system for measuring intraocular pressure (IOP) of an eye, comprising:
   a plurality of force sensors, said force sensors being adapted to contact a surface of an eye structure;
   means for measuring the forces exerted on said force sensors when said force sensors are in contact with said eye structure surface; and
   processing means for processing said measured forces, said processing means being adapted to receive said measured forces and programmed to determine intraocular pressure (IOP) of the eye as a function of said measured forces, wherein said IOP of the eye is determined by linear interpolation between two nearest force calibration curves representing first and second IOP values by the following relationship $$p = (p_a * a + p_b * b)/(a+b)$$

where:
$p_a$ and $p_b$ represent said first and second IOP values, and
a and b represent vertical distances to said calibration curves reflecting said $p_a$ and $p_b$.

3. The system of claim 2, wherein processing means is further adapted to determine outflow of aqueous humor from the eye as a function of said measured forces and measured changes in IOP over time.

4. The system of claim 3, wherein the following pressure-volume relationship is employed by said processing means to determine said outflow of aqueous humor $$V = \frac{4\pi r_0^3}{3}\left(\frac{p r_0 (1-v)}{2 t_0 E} + 1\right)^3.$$

5. The system of claim 2, wherein said system includes force sensor alignment means for aligning said force sensors.

6. The system of claim 2, wherein said system includes force sensor linear transmission means that is adapted to extend and retract each of said force sensors.

7. The system of claim 6, wherein said force sensor linear transmission means is further adapted to secure said force sensors in extended and retracted positions.

8. The method of claim 2, wherein said eye structure comprises the cornea.

9. The method of claim 2, wherein said eye structure comprises the sclera.

10. The method of claim 2, wherein said eye structure comprises adjoining eye tissue.

11. A method for determining intraocular pressure (IOP) of an eye, comprising the steps of:
   providing a palpation system having first and second force sensors, said first force sensor being in a first extended position and said second force sensor being in a first retracted position with respect to said first force sensor, said first and second force sensors being adapted to contact a surface of an eye structure, means for measuring forces exerted on said first and second force sensors when in contact with said eye structure surface, and processing means adapted to process said measured forces;
   placing said palpation system on said eye structure surface, whereby said extended first force sensor is in contact with said eye structure surface;
   applying a gradual first force to said eye structure surface with said palpation system and measuring force exerted on said first force sensor until said retracted second force sensor contacts said eye structure surface, whereby said second force sensor measures a first non-zero force; and
   determining IOP of said eye as a function of said force exerted on said first force sensor when said second force sensor contacts said eye structure surface.

12. The method of claim 11, wherein said IOP of the eye is determined by linear interpolation between two nearest force calibration curves representing first and second IOP values by the following relationship $$p = (p_a * a + p_b * b)/(a+b)$$

where:

$p_a$ and $p_b$ represent said first and second IOP values, and a and b represent vertical distances to said calibration curves reflecting said $p_a$ and $p_b$.

13. The method of claim 11, including the step of determining outflow of aqueous humor from the eye as a function of said measured forces and measured changes in IOP over time.

14. The method of claim 13, wherein the following pressure-volume relationship is employed to determine said outflow of aqueous humor $$V = \frac{4\pi r_0^3}{3}\left(\frac{pr_0(1-v)}{2t_0 E} + 1\right)^3.$$

15. The method of claim 13, including the step of subjecting said first and second force sensors to a first palpation sequence, said first palpation sequence comprising preprogrammed extension and retraction of said first and second force sensors.

16. A method for determining intraocular pressure (IOP) of an eye, comprising the steps of:
providing a palpation system having first and second force sensors, means for measuring forces exerted on said first and second force sensors when in contact with an eye structure surface, and processing means adapted to process said measured forces;
placing said palpation system on an eye structure surface, whereby at least one of said first and second force sensors is in contact with said eye structure surface;
subjecting said first and second force sensors to a first palpation sequence, said first palpation sequence comprising preprogrammed extension and retraction of said first and second force sensors;
measuring a first plurality of forces exerted on said first force sensor and a second plurality of forces exerted on said second force sensor over a first period of time and at a plurality of IOP values during said palpation sequence;
generating a plurality of calibration curves from said measured first and second plurality of forces; and
determining IOP of the eye based on said generated plurality of calibration curves.

17. The method of claim 16, wherein said IOP is determined by generating a test curve and performing a linear interpolation between said test curve and two nearest calibration curves.

18. The method of claim 17, wherein the following relationship is employed to determine said IOP $p=(p_a*a+p_b*b)/(a+b)$.

19. A method for determining fluid displacement out of an eye, comprising the steps of:
providing a palpation system having first and second force sensors, means for measuring forces exerted on said first and second force sensors when in contact with an eye structure surface, and processing means adapted to process said measured forces;
placing said palpation system on an eye structure surface, whereby at least one of said first and second force sensors is in contact with said eye structure surface;
subjecting said first and second force sensors to a first palpation sequence, said first palpation sequence comprising preprogrammed extension and retraction of said first and second force sensors;
measuring a first plurality of forces exerted on said first force sensor and a second plurality of forces exerted on said second force sensor over a first period of time and at a plurality of IOP values during said palpation sequence;
generating a plurality of calibration curves from said measured first and second plurality of forces;
determining IOP of the eye based on said generated plurality of calibration curves; and
determining fluid displacement out of the eye as a function of the determined IOP.

20. The method of claim 19, wherein said IOP is determined by generating a test curve and performing a linear interpolation between said test curve and two nearest calibration curves.

21. The method of claim 20, wherein the following relationship is employed to determine said IOP $p=(p_a*a+p_b*b)/(a+b)$.

22. The method of claim 19, wherein said step of determining said fluid displacement of the eye includes determining time rate of change of fluid volume in the eye as a function of said IOP.

* * * * *

UNITED STATES PATENT AND TRADEMARK OFFICE
CERTIFICATE OF CORRECTION

| | | |
|---|---|---|
| PATENT NO. | : 7,959,570 B2 | Page 1 of 1 |
| APPLICATION NO. | : 12/807101 | |
| DATED | : June 14, 2011 | |
| INVENTOR(S) | : Enikov et al. | |

It is certified that error appears in the above-identified patent and that said Letters Patent is hereby corrected as shown below:

Column 1, line 3, insert the following paragraph:

-- STATEMENT OF GOVERNMENT INTEREST

This invention was made with Government support under contract number 0603198 awarded by the National Science Foundation. The Government has certain rights in the invention. --

Signed and Sealed this
Eighteenth Day of October, 2011

David J. Kappos
*Director of the United States Patent and Trademark Office*